(12) United States Patent
Stuurman

(10) Patent No.: US 11,950,553 B2
(45) Date of Patent: Apr. 9, 2024

(54) COMPLEX TRAITS USING TISSUE TECHNOLOGY

(71) Applicant: Keygene N.V., Wageningen (NL)

(72) Inventor: Jeroen Stuurman, Wageningen (NL)

(73) Assignee: Keygene N.V., Wageningen (NL)

(*) Notice: Subject to any disclaimer, the term of this patent is extended or adjusted under 35 U.S.C. 154(b) by 36 days.

(21) Appl. No.: 16/449,329

(22) Filed: Jun. 21, 2019

(65) Prior Publication Data

US 2020/0045916 A1 Feb. 13, 2020

Related U.S. Application Data

(63) Continuation of application No. PCT/EP2017/084300, filed on Dec. 22, 2017.

(30) Foreign Application Priority Data

Dec. 23, 2016 (NL) .................................... 2018058

(51) Int. Cl.
*A01H 1/02* (2006.01)
*A01H 3/00* (2006.01)
*A01H 6/82* (2018.01)
*A01H 1/04* (2006.01)
*A01H 5/10* (2018.01)

(52) U.S. Cl.
CPC .............. *A01H 1/021* (2021.01); *A01H 3/00* (2013.01); *A01H 6/82* (2018.05); *A01H 1/04* (2013.01); *A01H 5/10* (2013.01)

(58) Field of Classification Search
CPC .................................... A01H 3/00; A01H 6/82
See application file for complete search history.

(56) References Cited

U.S. PATENT DOCUMENTS 8,183,434 B2 * 5/2012 Togami .............. C12N 15/8265
536/23.6

FOREIGN PATENT DOCUMENTS

EP 2 128 255 A1 12/2009

OTHER PUBLICATIONS

Kobayashi et al (Genome-Wide Analysis of Intraspecific DNA Polymorphism in 'Micro-Tom', a Model Cultivar of Tomato (*Solanum lycopersicum*). Plant Cell Physiol. 55(2): 445-454, 2014). (Year: 2014).*
Bolger et al (The genome of the stress-tolerant wild tomato species *Solanum pennellii*. Nature Genetics 46: 1034-1039, 2014). (Year: 2014).*
Yan et al (Pollen-mediated gene flow from transgenic cotton under greenhouse conditions is dependent on different pollinators. Nature Scientific Reports 1-9, 2015). (Year: 2015).*
Filippis et al. (Using a periclinal chimera to unravel layer-specific gene expression in plants. The Plant Journal 75, 1039-1049, 2013) (Year: 2013).*
University of Florida (Report of the Tomato Genetics Cooperative No. 56, 2006) (Year: 2006).*
Burge et al. "Opportunities for synthetic plant chimeral breeding: Past and future." Plant cell, tissue and organ culture 70.1 (2002): 13-21.
Filippis et al. "Using a periclinal chimera to unravel layer-specific gene expression in plants." The Plant Journal 75.6 (2013): 1039-1049.
International Search Report dated Mar. 8, 2018 for International Patent Application No. PCT/EP2017/084300 filed Dec. 22, 2017. 5 pages.
Lindsay et al. "Graft chimeras and somatic hybrids for new cultivars." New Zealand Journal of Botany 33.1 (1995): 79-92.
Nassar et al. "Interspecific Periclinal Chimeras as a Strategy for Cultivar Development." Plant Breeding Reviews 40 (2016): 235-269.
Nozawa et al. "Synthesis and utilization of in vitro artificially synthesized chimeras." Combined Proceedings of the International Plant Propagators' Society. vol. 52 (2002): 346.
Satina et al. "Demonstration of the three germ layers in the shoot apex of Datura by means of induced polyploidy in periclinal chimeras." American Journal of Botany 27.10 (1940): 895-905.
Szymkowiak et al. "The internal meristem layer (L3) determines floral meristem size and carpel number in tomato periclinal chimeras." The Plant Cell 4.9 (1992): 1089-1100.

* cited by examiner

*Primary Examiner* — Charles Logsdon
*Assistant Examiner* — Wayne Zhong
(74) *Attorney, Agent, or Firm* — Sunit Talapatra; Foley & Lardner LLP

(57) ABSTRACT

The present invention provides for a method for producing an inbred plant comprising a first and second trait of interest in the L1-shoot meristem layer for use in producing a periclinal chimera plant, the inbred plant thus obtained, the use of said inbred plant for producing said periclinal chimera plant, a method for producing a periclinal chimera plant using said inbred plant, a periclinal chimera plant thus obtained, the use of said periclinal chimera plant in producing plant product and the plant product thus obtained.

12 Claims, 24 Drawing Sheets

COMPLEX TRAITS USING TISSUE TECHNOLOGY

CROSS-REFERENCE TO RELATED PATENT APPLICATIONS

This application is a continuation of International Patent Application No. PCT/EP2017/084300, filed Dec. 22, 2017, which claims the benefit of and priority to Netherlands Application No. 2018058, filed Dec. 23, 2016. The entire disclosure of each application is incorporated by reference herein.

FIELD OF THE INVENTION

The present invention relates to the field of agriculture. In particular, the present invention relates to the production of plants with complex traits using tissue technology.

BACKGROUND OF THE INVENTION

The standard solution to enhance crop traits has been genetics and breeding. However, introducing a new trait in a commercially relevant variety by crossing (sexual hybridization) while maintaining (multigenomic and/or complex) commercially relevant traits such as fruit size and crop yield, requires a cumbersome and long term process or crossing and selection (introgression). Although genetic modification tools are available gaining a new trait in a relatively fast time span, these techniques are not widely accepted for modifying traits of (crop) plants. Therefore, there is a need for innovative, but commercially acceptable, ways to introduce traits in plants, in particular in crop plants.

Solution Provided by the Present Invention

The present inventors were the first to produce a commercially relevant crop plant harbouring a new trait in a significantly reduced time span as compared to state of the art crossing and selection, without making use of genetic modification techniques. The present inventors reached this goal by making use of tissue technology in combination with classical breeding techniques. By making use of tissue technology, the present invention seriously reduces the amount of required backcrossings and/or selfings and linkage drag problems. In fact, the present invention allows the production of phenotypes that would otherwise not exist.

In dicotyledonous plants, three separate layers of cells (L1-, L2- and L3-shoot meristem layer) are usually present in a shoot meristem. These separate shoot meristem layers result from a restricted directional cell division. The shoot meristem layers gives rise to all above-ground organs in an organized pattern: the outermost layer is the L1, the cells immediately below comprise the L2, and the inner tissues define the L3. The cells and tissues derived from the respective stem cells in the three cell layers of the shoot apical meristem have the respective genotypes of these stem cells in the three cell layers of the shoot apical meristems. Although spatially separated, these layers are integrated and communicate with each other (e.g. Curr Opin Plant Biol. 2008 February; 11(1); 42-48) Tissue technology methods, wherein one or two shoot meristem layers of a variety have been replaced by another, resulting in so called periclinal chimeras, have been used in the past to study differential gene expression and trait localization in these meristem layers (e.g. Filippis et al. Using a periclinal chimera to unravel layer-specific gene expression in plants, The Plant Journal, 2013, 75: 1039-1049). Further, preliminary investigations were done to investigate the usefulness of this technology in the provision of new cultivars, for instance by making chimera of nightshade and tomato using, however, with disappointing results (Lindsay et al. Graft chimeras and somatic hybrids for new cultivars, New Zealand journal of Botany, 1995, Vol. 33: 79-92).

The inventors now for the first time made use of these tissue technology methods to successfully produce a commercially relevant crop plant comprising a new trait in a relatively short time span. The inventors have identified certain traits to be localized in the L1-shoot meristem layer. By making use of tissue technology methods, the L1-shoot meristem layer of a first plant optimized to comprise such L1-localized trait of interest and preferably having a particular genotype as defined herein, can be combined with further shoot meristem layers of a commercially relevant second plant lacking said trait, to produce a commercially relevant periclinal chimera plant having the new trait of interest. As the first plant is not required to be optimized to be commercially relevant as a whole, the number of steps required to obtain a commercially relevant plant comprising a new trait of interest is significantly reduced. In addition, the invention provides a solution for the introduction of traits that are too complex to introgress.

SUMMARY OF THE PRESENT INVENTION

Clause 1.
A method for producing a periclinal chimera plant comprising a combination of at least a first and a second L1-localized trait of interest, wherein said method comprises the steps of:
  a) providing a first plant comprising said combination of L1-localized traits of interest;
  b) providing a second plant not comprising said combination of traits; and
  c) making a periclinal chimera plant comprising an L1-shoot meristem layer of the first plant and the L2 and L3-shoot meristem layer of the second plant.

Clause 2.
A method according to clause 1, wherein said first trait is an L1-localized trait from a wild species not comprising said second trait, and wherein said second trait is an L1-localized trait from a cultivar not comprising said first trait.

Clause 3.
Method according to clause 1 or 2, wherein said first trait is a biotic or abiotic stress resistance trait and said second trait is a fruit color trait and/or the ability to accept pollen that are produced by the second plant.

Clause 4.
A method according to any one of the preceding clauses, wherein said first plant is an F1-hybrid or inbred plant of a first parent plant comprising said first trait and a second parent plant comprising said second trait.

Clause 5.
A method according to any one of the preceding clauses, wherein the first plant is obtained by introducing at least one of the at least first and second L1-localized trait of the combination by genetic modification.

Clause 6.
Method according to any one of the preceding clauses, wherein the biotic or abiotic stress resistance is derived from any one of the group consisting of drought resistance, insect (whitefly) resistance, fungal (powdery mildew) resistance, oomycete (*phytophthora*) resistance, level and/or composition of acylsugar production, or any combination thereof.

Clause 7.
Method according to any one of the preceding clauses, wherein the one or more further L1-localized traits are selected from any one of the group consisting of fruit color, ability to accept pollen that are produced by the plant itself, and a combination thereof.
Clause 8.
Method according to any one of the preceding clauses, wherein the first plant is a commercially irrelevant plant, and wherein the second plant is of a commercially relevant variety or cultivar.
Clause 9.
Method according to any one of clauses 2-8, wherein the first parent plant is of a commercially irrelevant variety or a wild species, and wherein the second parent plant is a commercially relevant variety or cultivar.
Clause 10.
Method according to any one of the preceding clauses, wherein the first and second plant belong to genus *Solanum*.
Clause 11.
Use of a first plant comprising a combination of at least a first and a second L1-localized trait of interest as defined in any one of the preceding clauses, for providing an L1-shoot meristem layer in producing a periclinal chimera plant.
Clause 12.
Periclinal chimera plant obtainable by a method according to any one of clauses 1-10, or a plant vegetatively derived thereof.
Clause 13.
Use of a periclinal chimera plant as defined in clause 12, for producing a plant product.
Clause 14.
Method for producing a plant product from a periclinal chimera plant as defined in clause 12, wherein said method comprises the steps of:
 A) providing a periclinal chimera plant of clause 12;
 B) growing the periclinal chimera plant of step A);
 C) deriving a plant product from the plant grown in step B); and,
 D) optionally, further processing the plant product obtained in step C).
Clause 15.
Plant product obtainable by a method of clause 14.

S. *lycopersicum* (test plant); D: periclinal chimera with L2 and L3 from *S. lycopersicum* and L1 from F1 of *S. pimpinellifolium*×*S. lycopersicum* was transferred (test plant).

Figure 14:
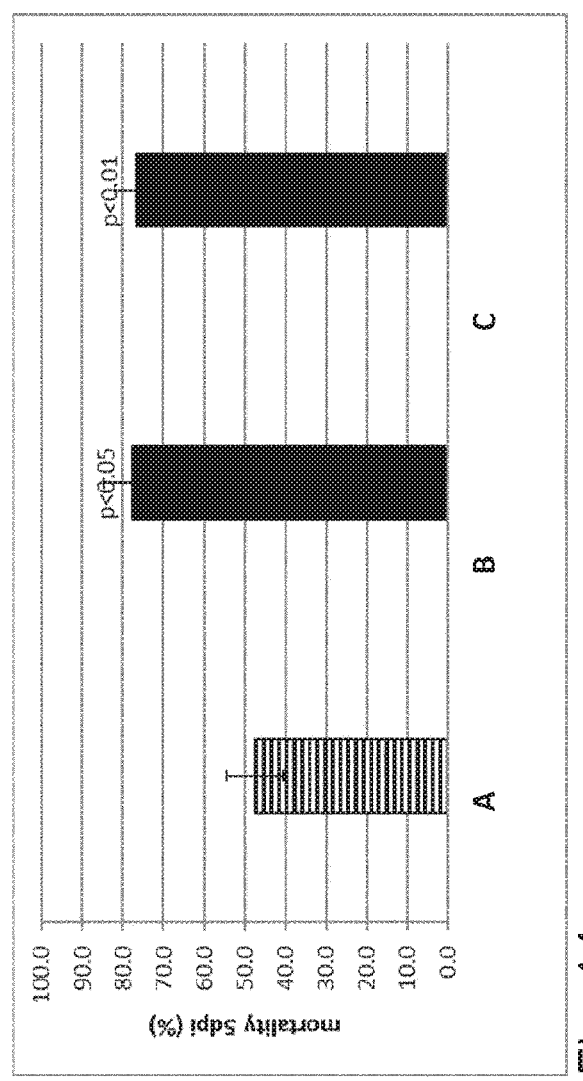

FIG. 14: *B. Tabaci* mortality after 5 days on three plant genotypes. A: *S. lycopersicum* (susceptible control); B: BC1S3 from a cross of *S. lycopersicum* with *S. pennellii*×*S. lycopersicum* was transferred (test plant); C: BC1S4 from a cross of *S. lycopersicum* with *S. pennellii*×*S. lycopersicum* was transferred (test plant).

Figure 15:
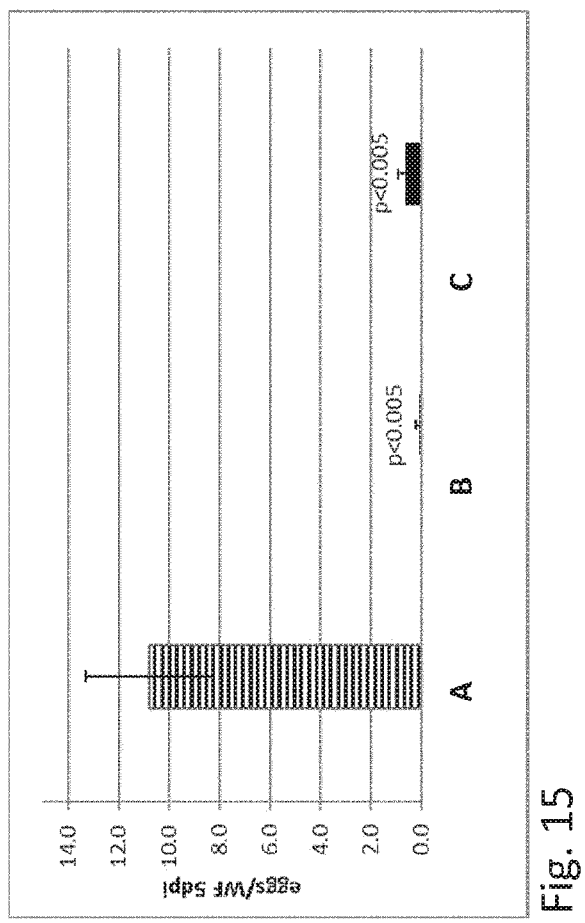

FIG. 15: Number of *B. Tabaci* eggs after 5 days on three plant genotypes (mean±stdev). A: *S. lycopersicum* (susceptible control); B: BC1S3 of *S. lycopersicum*×*S. pennellii* (donor plant); C: BC1S4 of *S. lycopersicum*×*S. pennellii* (donor plant).

Figure 16:
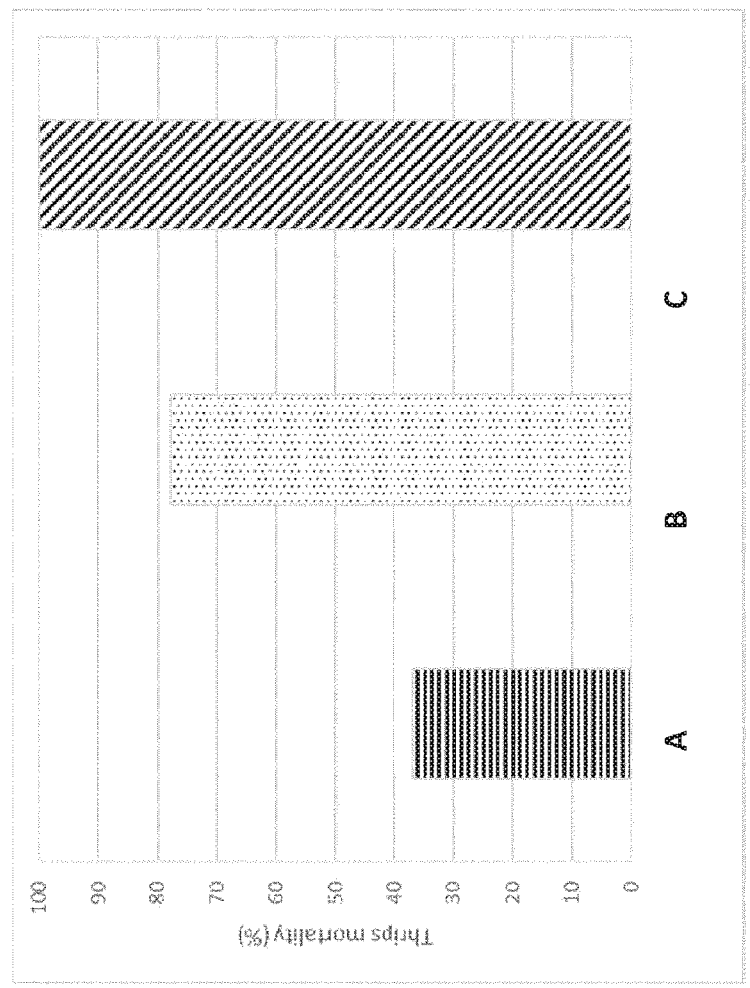

FIG. 16: Thrip mortality after 2 days on three plant genotypes. A: *S. lycopersicum* (susceptible control); B: F1 of *S. lycopersicum*×*S. pennellii* (donor plant); C: periclinal chimera with L2 and L3 from *S. lycopersicum* and L1 from F1 of *S. pennellii*×*S. lycopersicum* (test plant).

Figure 17:
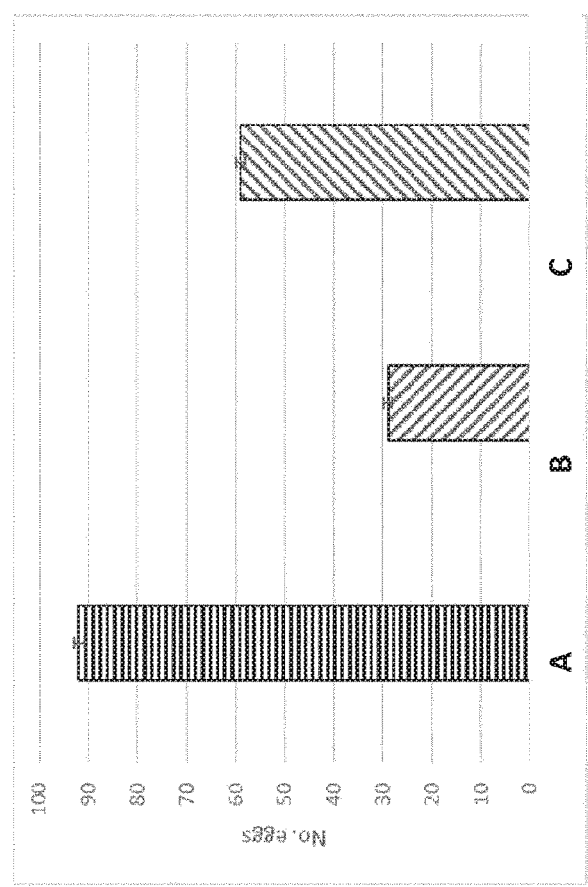

FIG. 17: Number of eggs deposited (mean±stdev) on three plant genotypes. A: *S. lycopersicum* (susceptible control); B: periclinal chimera with L2 and L3 from *S. lycopersicum* and L1 from F1 of *S. pennellii*×*S. lycopersicum* (test plant); C: periclinal chimera with L2 and L3 from *S. lycopersicum* and L1 from F1 of *S. habrochaites*×*S. lycopersicum* (test plant).

Figure 18:
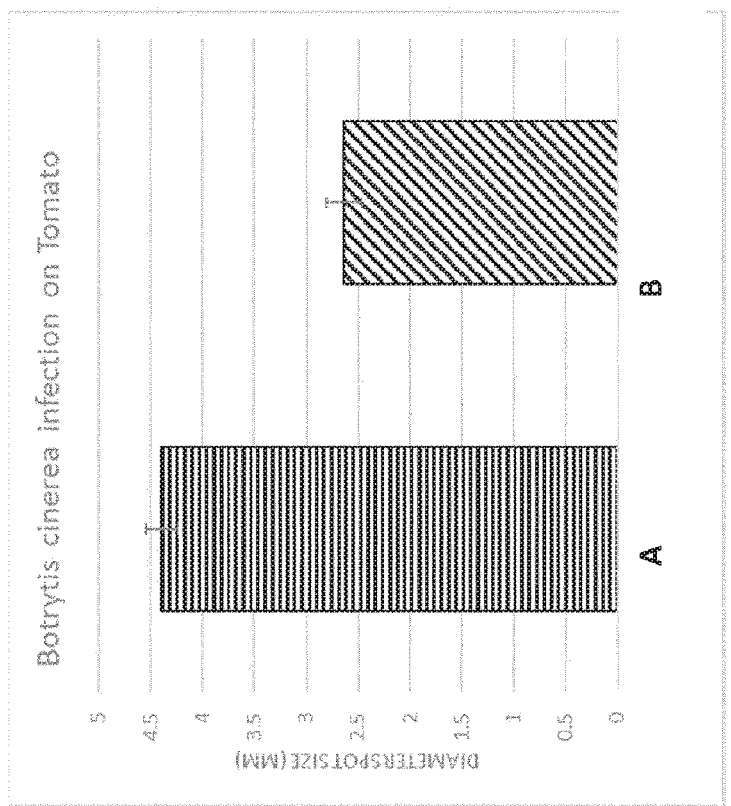

FIG. 18: Lesion diameter in mm (mean±stdev) on two plant genotypes. A: *S. lycopersicum* (susceptible control); B: periclinal chimera with L2 and L3 from *S. lycopersicum* and L1 from F1 of *S. habrochaites*×*S. lycopersicum* (test plant).

Figure 19:
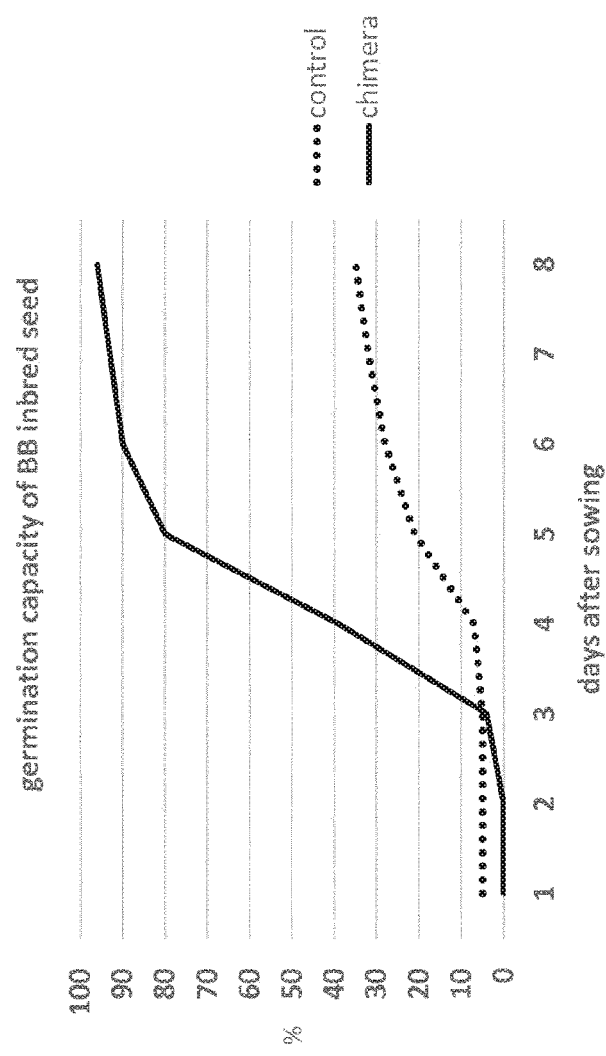

FIG. 19: In vitro germination capacity of BB seed produced by selfing a beef tomato plant (control) or a chimera comprising an L2 and L3 of beef tomato and L1 of F1 from cross Ailsa Craig×cherry-type *S. lycopersicum* inbred line (chimera: black line).

Figure 20:
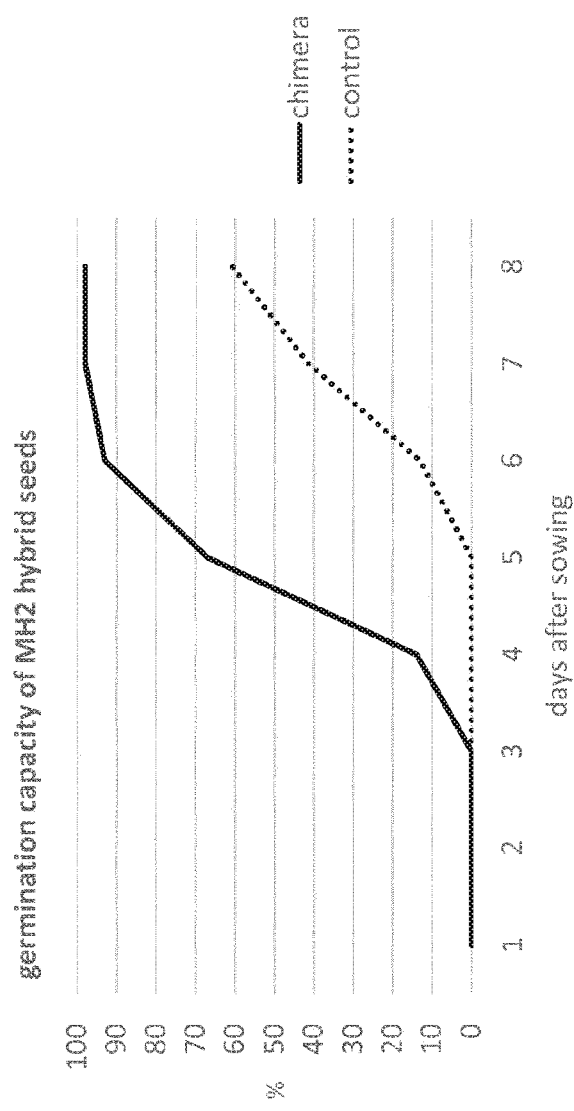

FIG. 20: In vitro germination capacity of MH2 seed. Black lines represent F1_chimera (chimera; progeny of the cross-fertilization of the chimera with line H2H2), grey lines represent F1_MM (control; progeny of the cross-fertilization of MM with line H2H2).

Figure 21:
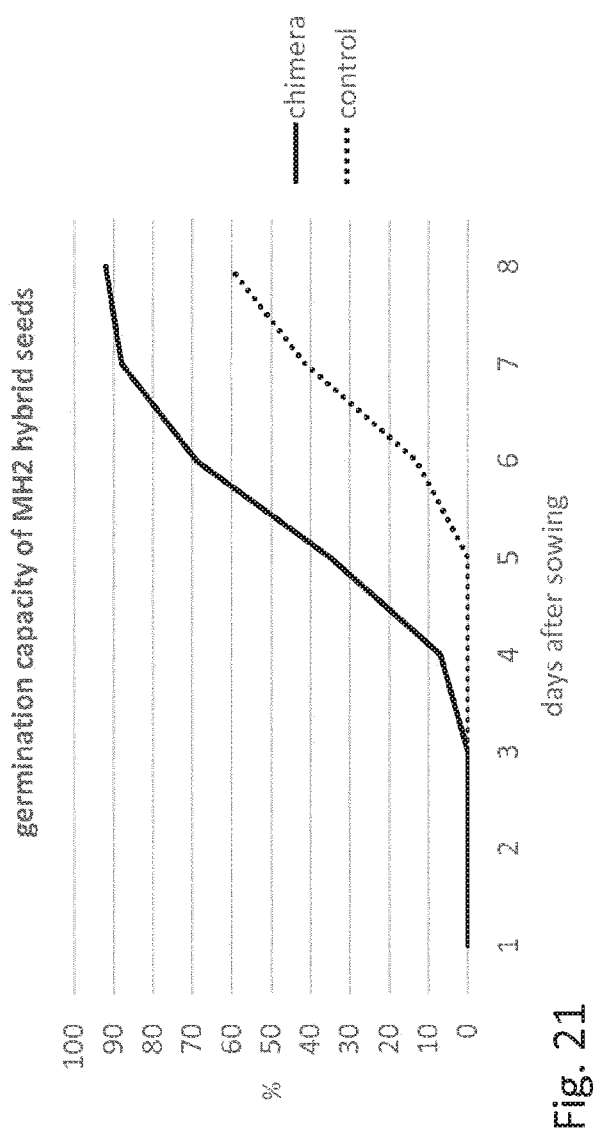

FIG. 21: In vitro germination capacity of MH2 seed. Black lines represent F1_chimera (chimera; progeny of the cross-fertilization of the chimera with line H2H2), grey lines represent F1_MM (control; progeny of the cross-fertilization of MM with line H2H2).

Figure 22:
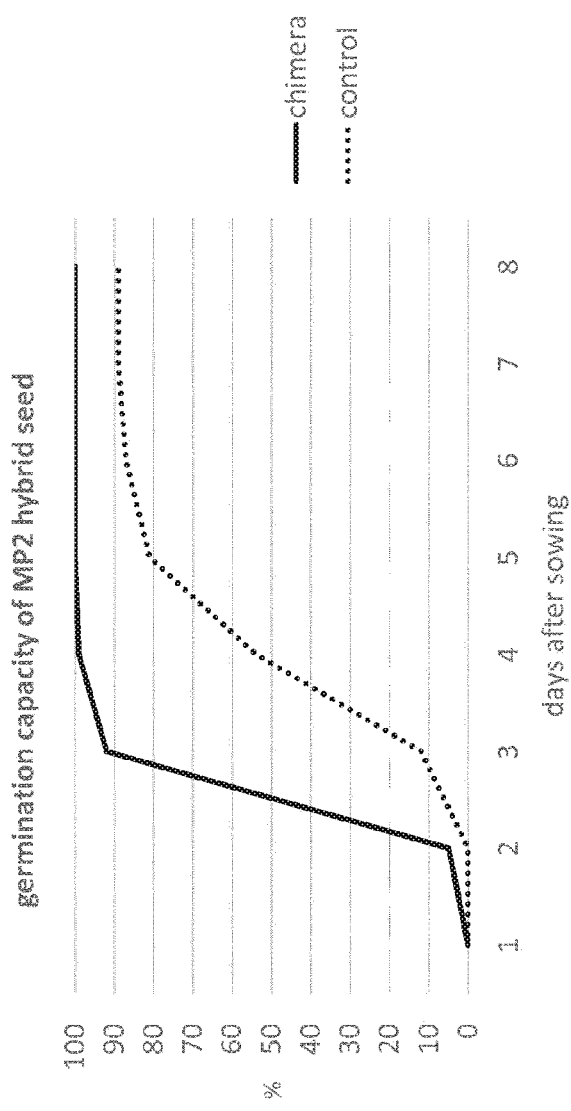

FIG. 22: In vitro germination capacity of MP2 seed. Black lines represent F1_chimera (chimera; progeny of the cross-fertilization of the chimera with line P2P2), grey lines represent F1_MM (control; progeny of the cross-fertilization of MM with line P2P2).

Figure 23:
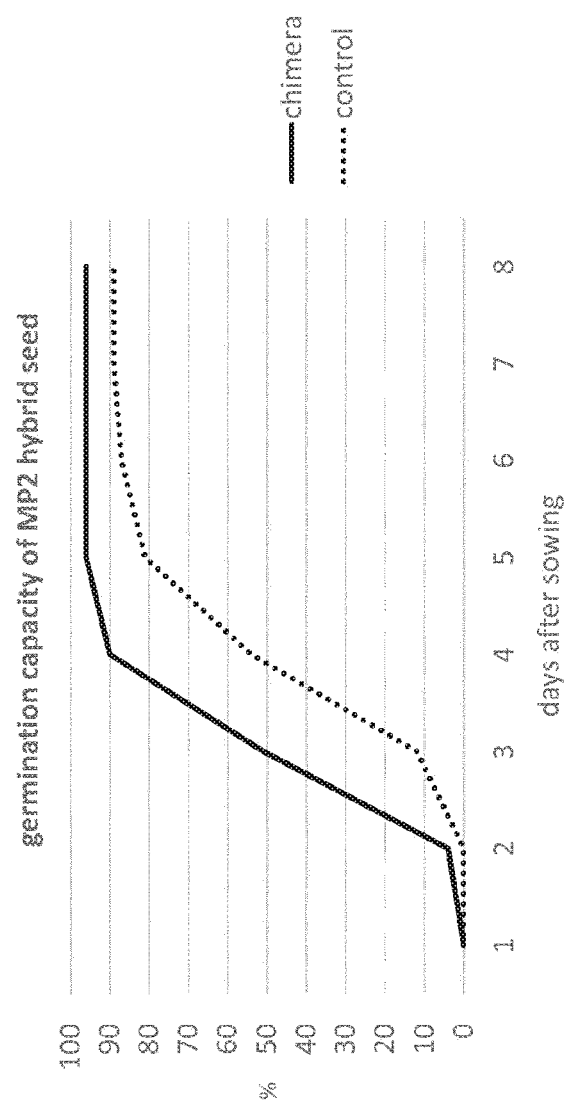

FIG. 23: In vitro germination capacity of MP2 seed. Black lines represent F1_chimera (chimera; progeny of the cross-fertilization of the chimera with line P2P2), grey lines represent F1_MM (control; progeny of the cross-fertilization of MM with line P2P2).

Figure 24:
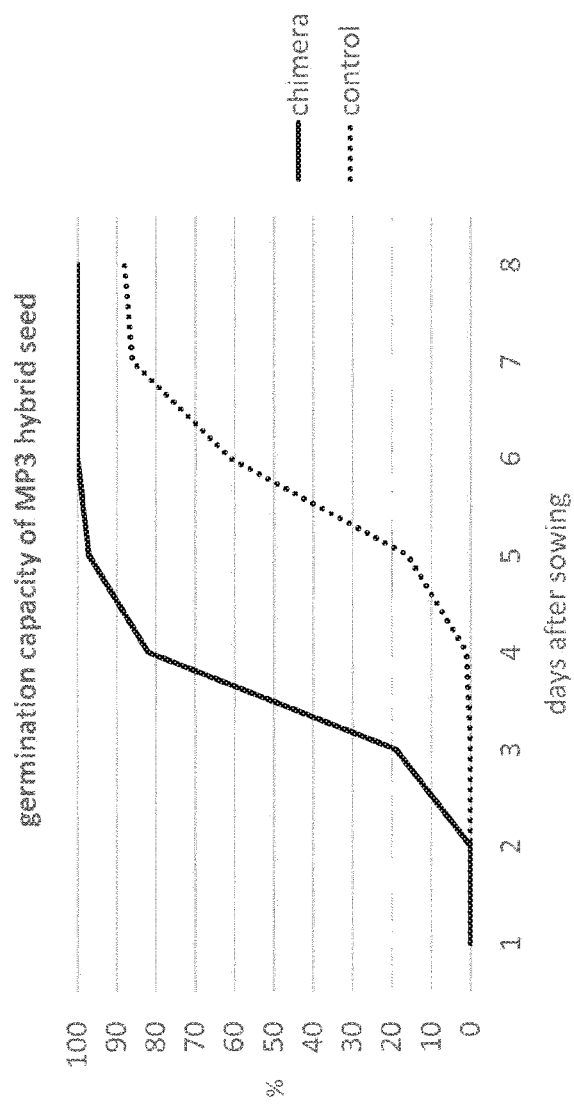

FIG. 24: In vitro germination capacity of MP3 seed. Black lines represent F1_chimera (chimera; progeny of the cross-fertilization of the chimera with line P3P3), grey lines represent F1_MM (control; progeny of the cross-fertilization of MM with line P3P3).

DESCRIPTION

Definitions

In the following description and examples, a number of terms is used. In order to provide a clear and consistent understanding of the specification and claims, including the scope to be given such terms, the following definitions are provided. Unless otherwise defined herein, all technical and scientific terms used have the same meaning as commonly understood by one of ordinary skill in the art to which this invention belongs.

As used herein, the terms "comprising" and "to comprise", and their conjugations, refer to a situation wherein said terms are used in their non-limiting sense to mean that items following the word are included, but items not specifically mentioned are not excluded. It also encompasses the more limiting verb "to consist of". In addition, reference to an element by the indefinite article "a" or "an" does not exclude the possibility that more than one of the element is present, unless the context clearly requires that there be one and only one of the elements. The indefinite article "a" or "an" thus usually means "at least one".

As used herein, the term "and/or" refers to a situation wherein one or more of the stated cases may occur, alone or in combination with at least one of the stated cases, up to with all of the stated cases.

"Inbreeding" is to be understood herein as the controlled self-fertilization, sibmating or backcrossing to a recurrent parent for at least 1, 2, 3, 4, 5, 6, 7, 8, 9 or 10, preferably at least 3, successive generations of controlled self-fertilization, sibmating or backcrossing to a recurrent parent. A plant resulting from inbreeding of an F1-hybrid plant self-fertilization, sibmating or backcrossing is denominated herein as an inbred plant.

As used herein, the term "trait" refers to a phenotypic trait, i.e. a property that is observable and measurable. A trait is determined by the expression of genes as well as environmental factors, and on interactions between gene expression and environmental factors. Examples of traits for plants are (but are not limited to): fruit size, fruit count, yield in kg per ha, plant height, relative growth speed, flowering time, improved seed germination, leaf area, disease and/or pest resistances, drought resistance, yield components and fruit colour. Preferably, the trait is a commercially-relevant trait. A further trait as defined herein is to be understood as a different trait that can be distinguished from one another on a phenotypic basis. Optionally, a trait can be assessed on a genotypic basis, taken that the gene(s) and/or polymorphisms responsible for said trait is/are known to the skilled person. Said one or more further traits as defined herein may be complex traits in the sense that multiple genes are involved and contribute to said trait. A "further trait" is to be understood as a second, third, fourth, fifth, sixth, seventh, eighth, ninth, tenth trait and so on. It can be desired that a trait is increased (improved) or decreased (deteriorated), and the respective shift of the average value for the characteristic in the population can improve the economic value of that a plant generation as compared to the parent generation(s). A plant is said to "comprise, exhibit, bear or have a trait" herein if that plant shows said trait significantly more or increased (e.g. at least 1%, 2%, 5%, 10%, 20%, 30%, 40% or more) as compared to a control plant (preferably the same or similar plant) that is not said to comprise, exhibit, bear or have said trait. An increase of a trait of a plant as relative to a control plant is determined under controlled environmental circumstances that are essentially identical or similar for both the plant of interest and the control plant. The skilled person is able to select controlled environmental circumstances or conditions measuring a trait.

"Similar environmental conditions" means among other things the use of a similar temperature, humidity, nutrition and light conditions, and similar irrigation, day/night rhythm and fertilization regimes. These conditions are for instance the conditions under which the plants that can be used in the method of the invention, including but not limited to, non-chimeric plants with the genotype of the stem cells of the L3-shoot meristem layer of the periclinal chimera or non-chimeric plants with the genotype of the stem cells of the L1-shoot meristem layer of the periclinal chimera are grown. Similar environmental conditions include identical environmental conditions.

A trait may be a "commercially relevant trait" if such trait is relevant for the economic value of a plant or plant variety, which is determined by the market and the type of plant or crop plant. The skilled person is aware what commercially relevant traits are under specific circumstances. For instance, if the plant is a crop plant, and the market requires a particular yield (in kg per ha) from said crop plant, sufficient yield can be considered as a commercially relevant trait. The skilled person is aware what will be considered "sufficient yield" for a particular crop plant under given circumstances. Further, if the plant is a fruit bearing plant and the market desires fruits to have a particular colour, this trait can be considered as a commercially relevant trait. A further commercially relevant trait of a fruit bearing plant may the ability to accept pollen that are produced by the plant itself, in order for the plant to set fruit, without the need to (manually) cross-pollinate the plants.

"Pest resistance" or "increased/enhanced pest resistance" is used herein to refer to an enhanced ability of plants (compared to a control plant not harboring the resistance) to withstand the attack of one or more plant pests, or in other words, it refers to a significant reduction in disease symptoms in plants compared to control plants. Pest resistance or enhanced pest resistance may be determined using a variety of methods. Often disease symptoms are scored visually (either in bioassays or in the field) by assessing the disease symptoms at one or more time points after infestation or contact with a pest (e.g. arthropod pest, insect pest, fungal pest, bacterial pest, oomycete or viral pest). Alternative methods include methods whereby the pest is detected and optionally quantified. A plant may thus show enhanced pest resistance if the amount or number of pests detected in/on the tissue is significantly less compared to controls, or if the pest spread is significantly slower than in controls. Ultimately, a significant increase in pest resistance (e.g. at least 1%, 2%, 5%, 10% or more) compared to controls, when grown under equivalent insect pest pressure (preferably in the field) provides an indirect measurement of enhanced pest resistance.

A "biotic stress resistance" or "pest resistance" may be resistance against a pest arthropod, pest fungus, pest bacterium, pest oomycete or pest virus. The pest arthropod may be, but is not limited to, Acari (spider mites, e.g. *Tetranychus urticae* and *Tetranychus evansi*), Lepidoptera (tissue-chewing caterpillars, e.g. *Tuta absoluta*), Coleoptera (tissue-chewing beetles, e.g. *Leptinotarsa decemlineata*), Hemiptera (sap-sucking aphids, e.g. *Macrosiphum euphorbiae*, or whitefly e.g. *Bemisia tabaci*, etc), Thysanoptera (cell content-feeding *thrips*, e.g. *Frankliniella occidentalis*) and Diptera (leaf-mining flies, e.g. *Liriomyza bryoniae*); the pest fungus may be, but is not limited to, *Oidium neolycopersici* (causing powdery mildew), *Cladosporium fulvum* (causing leaf mold), and *Botrytis cinerea* (causing grey mold); the pest bacterium may be, but is not limited to, *Xanthomonas vesicatoria* (causing bacterial leaf spot) and *Pseudomonas syringae* (causing bacterial speck); the pest oomycete may be *Phytophthora infestans* (causing late blight) resistance; and the pest virus may be, but is not limited to, Potato virus X and Pepino Mosaic Virus.

An "abiotic stress resistance" is used herein to refer to an enhanced ability of plants (compared to a control plant not harboring the resistance) to withstand the negative impact of one or more non-living (e.g. physical) factors on the living organisms in a specific environment, such as drought, osmotic stress and/or salinity, UV, cold, heat, xenobiotic treatment (e.g. herbicide and/or hormone), and mechanical stress. In other words, it refers to a significant reduction of an adverse reaction(s) or significant increased growth (e.g. yield) of plants under conditions of abiotic stress compared to control plants (preferably of a plant, not harboring the resistance).

An "L1-localized trait" is to be understood herein as a "trait localized in the L1-shoot meristem layer", which is a trait that is harbored essentially within the L1-shoot meristem layer, and is determined, at least essentially, by the genotype of the L1-shoot meristem layer, possibly together with one or more environmental factors. A trait localized in the L1-shoot meristem layer is passed to a periclinal chimera plant when using an L1-shoot meristem layer having this trait for producing the periclinal chimera plant, even if the L2 and/or L3-shoot meristem layers used for producing said periclinal chimera plant lack said trait. Examples of such traits are, but are not limited to, fruit color, pest resistance, drought resistance, ability to accept pollen that are produced by a particular plant, preferably the plant itself, and improved seed germination. Whether a trait is a trait localized in the L1-shoot meristem layer can be assessed by tissue techniques, i.e. by studying whether the trait comprised within a plant is transferred to a periclinal chimera plant that is prepared using the L1-shoot meristem layer of said plant comprising said trait and using the L2 and L3-shoot meristem layer of a plant not exhibiting said trait.

A "variety" is to be understood herein as a group of individuals or plants having similar traits that can be reproduced "true to type" from generation to generation.

A "commercially relevant plant or plant variety" is to be understood herein as a plant or plant variety that has sufficient commercially relevant traits to meet the demands of the market, i.e. to be of economic value. Such variety therefore comprises at least certain essential traits in order to be commercially relevant, depending on the crop species of said variety and further specific environmental circumstances such as climate. The skilled person is aware of such trait requirements of a commercially relevant variety. Such traits are defined herein above as commercially relevant traits.

A "commercially irrelevant plant or plant variety or plant species" is to be understood herein as a plant or variety or species that lacks at least one essential commercially relevant trait that is required to render the plant or variety or species to be commercially relevant. For instance, if a tomato plant lacks the ability to accept pollen that are produced by the plant itself, such tomato plant has no or insufficient economic value to be commercially relevant, as such plant requires hand-pollination.

A "cultivar" is to be understood herein as a commercially relevant variety that is produced by human intervention, i.e. by breeding and selection for desirable traits.

A "wild species" is a plant species that has developed and occurs naturally, i.e. without human intervention of breeding and selection.

A "crop plant" is to be understood herein as a plant that is harvested for food, clothing, livestock, fodder, biofuel, medicine, or other uses such as ornamental uses.

The term "offspring", refers to the first or further generation obtained by intercrossing. The F1-hybrid is to be understood herein as the first generation offspring resulting from a cross of genetically distinct individuals, preferably of a cross between two plants from distinct varieties, or from a cross between a cultivar and a wild species.

The term "phenotype" refers to the composite of an individual's traits, such as, but not limited to morphological, physical, biochemical, developmental or behavioural traits, which is therefore determined by the expression of genes as well as environmental factors, and on interactions between gene expression and environmental factors.

As used herein, the term "genotype" refers to the genetic makeup of a cell, an organism, or an individual (i.e. the specific allele makeup of the individual) usually with reference to a specific character or phenotypic trait of interest under consideration. However, not all organisms with the same genotype necessarily look or act the same way because appearance and behavior are modified by environmental and developmental conditions. Likewise, not all organisms that look alike necessarily have the same genotype.

As used herein, the term "genotyping" or "determining the genotype" refers to the process of determining genetic variations among individuals in a species. Single nucleotide polymorphisms (SNPs) are the most common type of genetic variation that are used for genotyping and by definition are single-base differences at a specific locus that is found in more than 1% of the population. SNPs are found in both coding and non-coding regions of the genome and can be associated with a phenotypic trait of interest such as a quantitative phenotypic trait of interest. Hence, SNPs can be used as markers for quantitative phenotypic traits of interest. Another common type of genetic variation that are used for genotyping are "InDels" or insertions and deletions of nucleotides of varying length. For both SNP and InDel genotyping, many methods exist to determine genotype among individuals. The chosen method generally depends on the throughput needed, which is a function of both the number of individuals being genotyped and the number of genotypes being tested for each individual. The chosen method also depends on the amount of sample material available from each individual or sample. For example, sequencing may be used for determining presence or absence of markers such as SNPs, e.g. such as Sanger sequencing and High Throughput Sequencing technologies (HTS). Sanger sequencing may involve sequencing via detection through (capillary) electrophoresis, in which up to 384 capillaries may be sequence analysed in one run. High throughput sequencing involves the parallel sequencing of thousands or millions or more sequences at once. HTS can be defined as Next Generation sequencing, i.e. techniques based on solid phase pyrosequencing or as Next-Next Generation sequencing based on single nucleotide real time sequencing (SMRT). HTS technologies are available such as offered by Roche, Illumina and Applied Biosystems (Life Technologies). Further high throughput sequencing technologies are described by and/or available from Helicos, Pacific Biosciences, Complete Genomics, Ion Torrent Systems, Oxford Nanopore Technologies, Nabsys, ZS Genetics, GnuBio. Each of these sequencing technologies have their own way of preparing samples prior to the actual sequencing step. These steps may be included in the high throughput sequencing method. In certain cases, steps that are particular for the sequencing step may be integrated in the sample preparation protocol prior to the actual sequencing step for reasons of efficiency or economy. For instance, adapters that are ligated to fragments may contain sections that can be used in subsequent sequencing steps (so-called sequencing adapters). Primers that are used to amplify a subset of fragments prior to sequencing may contain parts within their sequence that introduce sections that can later be used in the sequencing step, for instance by introducing through an amplification step a sequencing adapter or a capturing moiety in an amplicon that can be used in a subsequent sequencing step. Depending also on the sequencing technology used, amplification steps may be omitted.

As used herein, the term "molecular marker technique" refers to a (DNA based) assay that indicates (directly or indirectly) the presence or absence of a marker allele of interest in an individual (crop) plant. Preferably, it allows one to determine, e.g. by sequencing, whether a particular allele is present or absent at one of the positions at the locus in any individual.

As used herein, the term "locus" or "loci" (plural) refers to a specific site (place) or sites on the genome. For example, the "locus" refers to the site in the genome where the two alleles of the locus are found (for diploid organisms), or a multiple hereof in the case of polyploid individuals or plants. Quantitative trait loci (QTLs) are sites on the genome containing alleles that are associated to a quantitative trait (based on the genotype/phenotype relationship model).

The term "allele" refers to the nucleotide sequence variant that is present on one of the positions of a particular locus. A diploid individual has two positions for one allele per locus, one position on either one of the two homologous chromosomes. For each of the positions of a particular locus, one or more alternative nucleotide sequence variants may exist in a population, i.e. for each position different possible alleles may exist in a population. However, each individual can have only one of the possible alleles on each one of the positions of a locus. The alternative nucleotide sequence variants, i.e. the different possible alleles, differ at least slightly in nucleotide sequence, and typically can be distinguished based on the presence or absence of at least one SNP or InDel. When referred herein to an "allelic state", reference is made to the presence or absence of an allele at a position within a particular locus, which can be expressed as the presence or absence of the respective marker (e.g. SNP or indel) at the particular locus.

As used herein, the term "heterozygous" refers to a genetic condition existing when two different alleles reside at a specific locus, for example a locus having alleles A/B, wherein A and B are positioned individually on either one of the two homologous chromosomes. Conversely, as used herein, the term "homozygous" refers to a genetic condition existing when two identical alleles reside at a specific locus, for example a locus having alleles A/A, positioned individually on either one of the two homologous chromosomes.

"Periclinal chimeras" are chimeras in which one or more entire cell (tissue) layer(s) L1, L2, and/or L3 is genetically distinct from another cell layer. In the case of periclinal chimeras, a single tissue layer itself is homogeneous and not chimeric. Periclinal chimeras are the most stable forms of chimeras, and produce distinctive and valuable plant phenotypes. These plants produce axillary buds that possess the same apical organization as the terminal meristem from which they were generated. Therefore, periclinal chimeras can be multiplied by vegetative propagation and maintain their chimera layer organization. Periclinal chimeras can be made by somatic mutagenesis of stem cells in one of the (L1-, L2-, L3-) layers of the shoot meristem. Periclinal chimeras can also be produced by synthetic methods, for example as described by Szymkowiak, E. J., and Sussex, I. M. (1992), The internal meristem layer (L3) determines floral meristem size and carpel number in tomato periclinal chimeras, Plant Cell 4, 1089-1100. Said periclinal chimeras are an example of interspecific cell layer transplantations occurring between the two grafted species. This particular method is practiced under ambient conditions, in a growth room or greenhouse. It consists of regular grafting of two plants, one as rootstock and another as scion. Graft unions, after healing, are cut and allowed to regenerate adventitious shoots. Among these adventitious shoots, chimeras can appear spontaneously. In vitro synthetic techniques have also been developed to produce periclinal chimeras. These include: (1) co-culturing of cells, wherein adjoined stem slices from two different plants are cultured together into chimeral callus, and adventitious chimeric shoots are regenerated from these calli on hormone-supplemented in vitro growth media. (2) mixed callus cultures, wherein cell-suspensions of two different plants are mixed, the mixtures are grown into chimeral callus, and adventitious chimeric shoots are regenerated from these calli on hormone-supplemented in vitro growth media. (3) co-culture of protoplasts, wherein protoplast suspensions of two different plants are embedded in agarose and grown to very high cell densities, upon which chimeric shoot are regenerated on hormone-supplemented in vitro growth media. (4) in vitro graft culture, wherein two seedlings are grafted along their hypocotyls under sterile conditions, and sub-apical cross sections of the grafts are cultured to induce chimeric adventitious calli and shoots. Such techniques fall under the common denominator of tissue culture, and consist of a multitude of distinct protocols that may be specific for individual plant lines or species. The skilled person will know how to bring cells of two different plants together in tissue culture, to regenerate plants which may or may not be periclinal chimeras. For an elaborate review on plant chimeras, see "Plant Chimeras" by Richard A. E. Tilney-Bassett (Cambridge University Press, 1991).

"Solanaceae" refers herein to plant genera, species, and varieties thereof, belonging to the family Solanaceae. These include species belonging to the genus *Solanum* (including *Solanum lycopersicum*, which used to be known as *Lycopersicon esculentum*), *Nicotiana, Capsicum, Petunia* and other genera.

All patent and literature references cited in the present specification are hereby incorporated by reference in their entirety.

DETAILED DESCRIPTION

It is contemplated that any method, use, plant or plant product described herein can be implemented with respect to any other method, use, plant or plant product described herein. Embodiments discussed in the context of methods, use, plant and/or plant product of the invention may be employed with respect to any other method, use, plant or plant product described herein. Thus, an embodiment pertaining to one method, use, plant or plant product may be applied to other methods, uses, plants and plant products of the invention as well.

Provided is a method for producing a periclinal chimera plant comprising an L1-localized trait of interest, wherein said method comprises the steps of:
  a) providing a first plant comprising said L1-localized trait of interest;
  b) providing a second plant not comprising said L1-localized trait of interest; and
  c) making a periclinal chimera plant comprising an L1-shoot meristem layer of the first plant and the L2 and L3-shoot meristem layer of the second plant.

Preferably the method of the invention is for producing a periclinal chimera plant comprising a combination of L1-localized traits of interest, wherein said method comprises the steps of:
  a) providing a first plant comprising said combination of L1-localized traits of interest;
  b) providing a second plant not comprising said combination of L1-localized traits of interest; and
  c) making a periclinal chimera plant comprising an L1-shoot meristem layer of the first plant and the L2 and L3-shoot meristem layer of the second plant.

Also provided is the first plant as defined herein and the use of said first plant for producing a periclinal chimera plant comprising the L1-shoot meristem layer of said first plant.

A combination of L1-localized traits of interest is to be understood as a combination of at least two L1-localized traits of interest, in other words, said combination comprises at least a first and a second L1-localized trait of interest.

In an embodiment, said first trait is an L1-localized trait derived or derivable from a first parent plant not comprising said second trait, and said second trait is an L1-localized trait derived or derivable from a second parent plant not comprising said first trait. The first parent plant and the second parent plant can be inbred lines, cultivars and/or wild accessions or species. In a preferred embodiment, said first trait is an L1-localized trait derived or derivable from a wild species not comprising said second trait, and said second trait is an L1-localized trait derived or derivable from a cultivar not comprising said first trait. Such wild species and cultivars are defined further herein. The inventors have identified several L1-localized traits in wild species that are valuable to have as a trait in a plant comprising further L1, L2 and/or L3-localized traits not comprised in said wild species, e.g. a trait that is present in a cultivar. Particular L1-localized traits present in wild species are biotic and abiotic stress resistance traits. Particular L1-localized traits of in present in cultivars are fruit color and the ability to accept pollen that are produced by a particular plant, preferably the second plant as defined herein. These and other L1-localized traits are detailed further herein. In a preferred embodiment, said combination of L1-localized traits of interest does not occur in a single plant or plant species in nature, i.e. without human intervention such as crossing and selection, genetic modification and/or tissue technology. In other words, the occurrence of said combination preferably requires human intervention in order to appear in a single plant or plant variety.

Optionally, the combination of L1-localized traits of interest is a combination of at least 2, 3, 4, 5, 6, 7, 8, 9, 10 or more L1-localized trait of interest.

The combination of L1-localized traits of interest may be introduced in the first plant by crossing and selection or by genetic modification.

For instance, the first plant may be obtainable or obtained from crossing a first parent plant comprising the first trait of interest with a second parent plant comprising second trait of interest, optionally followed by several rounds of inbreeding, in order to obtain a plant comprising the combination of the first and second L1-localized traits of interest. Such method of crossing and selection is in particular preferred in case the first and/or second traits are complex traits. It is understood in the art of crop science that multiple, often complex traits are required in order for a plant to be commercially relevant. Introduction of a new trait requires many steps of crossing and selection in order to arrive at a commercially relevant plant. The inventors came to the insight that an important advantage of introducing a new L1-localized trait of interest in a plant via the production of a periclinal chimera requires significantly less crossing and selection steps in order to arrive at a commercially relevant plant. Using the method of the invention, crossing and selection may be performed until a commercially relevant L1-shoot meristem layer is obtained, i.e. comprising a combination of the new trait of interest and one or more further commercially relevant L1-localized traits, while the plant as a whole may still show unfavorable properties or lack commercial properties that are relevant for instance for crop plants, as this will be compensated for by the L2 and L3 layer of the second plant.

Therefore, step a) of the method of the invention may be preceded by crossing a first parent plant with a second parent plant, optionally followed by several rounds of inbreeding, under the selection of the combination of L1-localized traits of interest.

In other words, the invention also provides for a method for producing a first plant comprising the combination of L1-localized traits of interest, wherein said method comprises the steps of:
- a1) providing a first parent plant comprising the first L1-localized trait of interest;
- a2) providing a second parent plant comprising the second L1-localized trait of interest;
- a3) crossing the first parent plant with the second parent plant in order to obtain F1-hybrid, and optionally inbreeding of said F1-hybrid;
- a4) selecting an F1-hybrid or inbred plant of step a3), that comprises the combination of the first and the second L1-localized traits of interest.

Therefore, the first plant as defined in the method for producing a periclinal plant may be an F1-hybrid or an inbred plant. Preferably, said first plant is an F1-hybrid or inbred plant of a first parent plant comprising said first trait and a second parent plant comprising said second trait. Also provided is the F1-hybrid or inbred plant obtained or obtainable by the method above, characterized in that it comprises the combination of the first and the second L1-localized traits of interest. This F1-hybrid or inbred plant may be used, is for use, or is suitable for use, in producing a periclinal chimera plant comprising the L1-shoot meristem layer of said F1-hybrid or inbred plant. Therefore, also provided is the use of said F1-hybrid or inbred plant for producing a periclinal chimera plant comprising the L1-shoot meristem layer of said hybrid or inbred plant.

The method of producing a periclinal chimera plant as defined herein above, may comprise the method of producing the first plant as defined above. More in particular, step a) of the method of producing a periclinal chimera plant as defined herein my above may comprise method steps a1)-a4) as defined herein in the method of producing the first plant. The first and second plant preferably have different genotypes. Further, the first parent plant and the second parent plant preferably have different genotypes. Optionally, the first parent plant may be a wild species and the second parent plant may be a commercially relevant variety or cultivar. The first parent plant may be a wild species naturally comprising said first trait and said second plant may be a cultivar comprising said second trait. Specific traits identified by the inventors to be localized in the L1-shoot meristem layer of wild species are particular biotic and abiotic stress resistances and improved seed germination quality, in particular improved seed germination quality of seed having the genotype of a cross of said wild species with a cultivar. Particular traits localized in the L1-shoot meristem layer of a cultivar are the trait of fruit having a particular color (i.e. red fruit in case of tomato) and/or the ability to accept pollen that are produced by a particular plant, preferably the second plant as defined herein, which is preferably a cultivar. Such L1-localized traits present in cultivars but lacking in wild species preferably are commercially relevant traits as defined herein.

In the method for producing a first plant as defined herein above, the wild species may be crossed with a cultivar followed by several rounds of inbreeding under the selection of at least said first trait. Optionally the F1-hybrid of said method already comprises the combination of L1-localized traits of interest. In that case, no further inbreeding is required. Optionally, the F1-hybrid of the method above does not comprise all L1-localized traits of the combination. In the latter case, inbreeding of the F1-hybrid is preferred in order to obtain an inbred plant comprising the combination of L1-localized traits of interest.

Inbreeding may be continued until an inbred plant is obtained comprising the combination of L1-localized traits of interest. Optionally, inbreeding is continued until an inbred plant is obtained that is genetically fixed for said combination. Optionally, inbreeding in the method as defined above is under the continuous selection for all L1-localized traits of the combination. In other words, after each round of crossing or inbreeding, offspring is selected for further inbreeding based on the presence of all of the L1-localized traits of the combination. Alternatively, selection may be performed after several rounds of inbreeding. Optionally, after each round of inbreeding, offspring is selected for further inbreeding based on at least one trait of the combination, while the selection based on further traits is performed after several rounds of inbreeding. Preferably at least 1, 2, 3, 4, 5, 6, 7, 8, 9 or 10, preferably at least 3, successive rounds of inbreeding is performed. Preferably, no more than 10, 9, 8, 7, 6, 5, 4 or 3 successive rounds of inbreeding is performed.

Optionally, the first plant is a plant, wherein the genotypic contribution of the second parent plant to the total genotype of the first plant is at least 0.5%, preferably at least 2%, 5%, 10%, 20%, 30%, 40%, 50%, 60% or at least 70%. Optionally, the first plant is a plant, wherein the genotypic contribution of the first parent plant to the total genotype of the first plant is at least 0.5%, preferably at least 2%, 5%, 10%, 20%, 30%, 40%, 50%, 60% or at least 70%.

As indicated above, optionally, the combination of L1-localized traits of interest of the first plant as defined herein is a combination of at least 2, 3, 4, 5, 6, 7, 8, 9, 10 or more L1-localized traits of interest. Optionally, part of these traits originate from the first parent plant, and part originate from the second parent plant. For instance, the first parent plant may comprise both a combination of biotic and/or abiotic stress resistances, while the second parent plant comprises one or more L1-localized traits such as fruit color and/or ability to accept pollen produced by the second plant. Optionally, the first plant comprises the combination of a biotic and/or abiotic stress resistance with one or more improved seed germination properties (preferably of seed having the a particular desired genotype), while the second parent plant comprises may one or more traits such as fruit color and/or ability to accept pollen produced by the second plant.

The second plant providing the L2- and L3-shoot meristem layer of the periclinal chimera plant as defined herein, may be a plant that is different from any one of the first plant or first and second parent plant as defined herein above. Preferably, the second plant is a plant not comprising the combination of L1-localized traits of interest as defined above. Preferably, the second plant comprises at least sufficient traits in order to classify the plant as commercially relevant. Optionally, the second plant does not comprise the first trait of interest derived from the first parent plant as defined above, but may comprise the second and optionally further traits derived from the second parent plant as defined above. The second plant may be of the same variety as the second parent plant as defined above. The second plant may have the same genotype as said second parent plant.

In a further embodiment, the first plant is produced by making use of genetic modification. Making use of genetic modification for introducing a trait of interest is in particular preferred in case the gene(s) associated with said trait have been identified. Preferably, said trait is a simple trait that can be introduced by altering the expression of a single gene or by altering the nucleotide sequence of a gene, or preferably even by altering a single nucleotide within said gene. A combination of genetic modification techniques and crossing and selection as defined herein above is also encompassed by the present invention. Optionally, at least one of the L1-localized traits of the combination as defined herein is introduced in a plant by genetic modification, wherein said plant already comprises one or more further L1-localized traits of the combination. Such method may be free of classical breeding and/or selection techniques. It is also encompassed by the present invention that at least one of the L1-localized traits of the combination as defined herein is introduced in a plant via genetic modification. Said at least one trait may be introduced before or after crossing and/or inbreeding of the first and second parent plant as defined herein. Taken together, combinations of crossing and selection and genetic modification for producing the first plant are envisaged and encompassed in the present invention. An important advantage of a periclinal chimera produced using a genetically modified first plant for providing the L1-shoot meristem layer of said chimer, is that the gametes produced by said chimera are derived from the genotype of the second plant and may therefore be considered free of genetic modification, taken that the second plant is free of genetic modification. A further benefit is that an allele may have beneficial phenotypic effects in one layer (e.g. L1), but may cause pleiotropic effects in other layers (e.g. L2 and L3). Such pleiotropic effects of an allele may be circumvented by using the tissue technology of the present invention, and producing a periclinal chimera plant by the method of the invention. An example of such periclinal chimera is a chimera comprising an L1 layer from *S. lycopersicum* plant that has an epidermal specific (L1) knock-out of the homolog of Mildew Locus O or DMR6 (downy mildew resistance 6), further comprising an L2 and L3 from *S. lycopersicum* expressing the wild type of said homolog. Such plants will be assessed for resistance to Solanaceae-specific mildew diseases or other pathogens with a biotrophic life-style, such as *Oidium neolycopersici* (Nekrasov et al., 2017) and *Phytophthora capsici* (de Teledo Thomazella et al., 2016), respectively.

Methods for genetic modification encompassed by the present invention are methods resulting the modification of the gene or genes associated with the trait of interest. Such modification may be, but is not limited to, the incorporation, deletion or altering of any one of the nucleotide sequences of said gene(s) to be modified using routine random or targeted mutagenesis methods. The latter including without limitation, those employing zinc finger nucleases, Cas9-like, Cas9/crRNA/tracrRNA or Cas9/gRNA CRISPR systems, or targeted mutagenesis methods employing mutagenic oligonucleotides (e.g., KeyBase® or TALENs). Altering may be inserting, deleting and/or replacing at least one nucleotide. Such modification may also be the transient or stable incorporation of a vector, such as an expression vector, e.g. a silencing vector, or other construct into a plant, plant cell, or plant protoplast. Such expression vector may be a vector for the overexpression or de novo expression of a gene(s) associated with the trait of interest. Such vector may also be a vector to silence (e.g. an RNAi expression construct), knock down or knock out (e.g. by T-DNA insertion) the gene(s) associated with the trait of interest. Optionally such vector comprises a tissue specific promoter, which preferably is an epidermal specific promoter, such as a trichome specific or stomata specific promoter. Preferably, said promoter is operably linked to the sequence required for the genetic modification, such as the sequence encoding the gene to be (over- or de novo) expressed, sequence encoding the enzyme for targeted mutagenesis, or the sequence encoding for RNAi.

Genes of interest to be (over- or de novo) expressed in said first plant may be genes encoding for proteins that are pest toxins or repellents (e.g. toxins or repellents for certain insect or fungal pests), genes encoding for proteins or enzymes that are involved in the production of toxins or repellents for pest (e.g. terpenoids, terpenoid derivatives, methylketones and acylsugars) (see e.g., Kuai et al. Plant Physiol 1997, 115:1581-1587; Yu and Pichersky, Plant Physiol. 2014, 164(2): 612-622; Yu and Pichersky, Plant Physiol. 2014, 164(2): 612-622; Palma et al. Toxins (Basel). 2014, 6(12): 3296-3325; Schilmiller et al. Plant Physiol. 2016, 170(3): 1331-1344), wax production (Lee and Suh, Plant Cell Rep. 2015; 34(4): 557-572; Chang et al. Theor Appl Genet. 2016; 129(8):1531-1539; Yang et al. Proc Natl Acad Sci USA. 2011 Jul. 19; 108(29):11836-11841; Tian et al. Planta. 2012; 236 (4): 1053-1066), genes trichome formation (Kang et al. J Exp Bot. 2016; 67(18): 5313-5324) and/or stomata formation. Further of interest are constructs resulting or encoding for RNAi targeting insect-specific genes crucial to their development (Gordon and Waterhouse, Nat Biotechnol. 2007; 25(11): 1231-1232).

The second plant providing the L2- and L3-shoot meristem layer of the periclinal chimera plant as defined herein, may be a plant that is of the same species or variety as the first plant that is used for producing the genetically modified first plant. The second plant may have the same genotype as the first plant before the introduction of the L1-localized trait of interest or combination of L1-localized traits of interest by the genetic modification, i.e. the plant or plant cell or protoplast used as starting material for the genetic modification.

The first plant, second plant, first parent plant and second parent plant as defined above may belong to the family Solanaceae, preferably to the genus *Solanum*. A commercially relevant plant or cultivar may be a cultivated tomato plant, preferably of a variety of *Solanum lycopersicum* (such as Ailsa Craig). A commercially irrelevant plant may be a wild tomato, preferably a species of *Solanum pennelli* (such as line LA716), *Solanum habrochaites* (such as accession PI127826), *Solanum galapagense* or *Solanum pimpinellifolium*. Preferably, the first parent plant is a plant of a wild tomato species, preferably of *Solanum pennelli*, and the second parent plant, and optionally the second plant, is a cultivar, preferably a plant of a variety of *Solanum lycopersicum*. Preferably, the first, second, first parent and/or second parent plant is not of the species *Solanum nigrum*.

The L1-localized trait of interest as defined herein may be, but is limited to, biotic or abiotic stress resistance, improved seed germination, fruit color and ability to accept pollen that are produced by the plant itself. Biotic stress resistance traits may be, but are not limited to resistance against arthropods, pest fungus, pest bacterium, pest oomycete and/or pest virus as defined herein. Biotic stress resistance traits may also encompass increased production of pest toxins or repellents such as terpenoids, terpenoid derivatives, methylketones and acylsugars (any of a group of sugars comprising glucose acylated with short and/or medium chain length fatty acids varying in length), and the increased production of wax.

The combination of L1-localized traits of interest as defined herein may be, but is not limited to, any combination of the following L1-localized traits: biotic stress resistance, abiotic stress resistance, improved seed germination as defined herein, fruit color and ability to accept pollen that are produced by the second plant as defined herein.

In a preferred embodiment, the first L1-localized trait of interest is a trait is comprised in a wild plant species, while the second L1-localized trait of the combination of L1-localized traits of interest as defined herein, is comprised in a cultivar. Preferably, said first trait is a biotic or abiotic stress resistance. The first trait may also be one or more improved seed germination properties, preferably improved germination properties of seed, wherein the seed embryo has a particular desired genotype such as the genotype of seed from a cross of said wild plant species with the second plant as defined herein. Preferably, said second trait from a cultivar is a commercially relevant L1-localized trait, such as, fruit color and/or the ability to accept pollen from the periclinal chimera plant itself and/or of the second plant as defined herein.

In a preferred embodiment, the first trait of interest is a biotic stress resistance. Preferably, the combination of L1-localized traits of interest is: a biotic stress resistance, preferably whitefly resistance, in combination with a particular color of fruit, preferably being red in case the fruits produced by the plant are tomatoes, and the ability to accept pollen from the periclinal chimera plant itself and/or of the second plant as defined herein. Optionally, the biotic stress resistance is comprised in a first parent plant as defined herein, which may be an accession of *S. pennellii*, while fruit color and the ability to accept pollen from the periclinal chimera plant itself and/or the second plant as defined herein is comprised in the second parent plant, which may be a cultivar of *S. lycopersicum*. Preferably, the first plant comprising the combination of these three L1-localized traits is obtained or obtainable by crossing said first and second parent plant and subsequently inbreeding the F1-hybrid obtained for at least 3 rounds. Preferably, the F1-hybrid is backcrossed three times with the second parent plant and selfed once in order to obtain a first plant that can be used for producing a periclinal chimera plant as defined herein.

As indicated above, selecting offspring or genetically modified plants is required in the method of the invention for producing a periclinal chimera and/or for producing a first plant as defined herein. The assessment of a dominant trait being passed to its offspring can be done phenotypically. However, in case of a recessive trait, whether such trait is passed to its offspring may need to be assessed genotypically (optionally via molecular marker technique) and/or phenotypically at a later stage, i.e. after one or more further crossing steps (inbreeding) resulting in a homozygous genotype of that recessive trait.

Selection based on genotypes preferably requires a direct and known link of the phenotypic trait of interest and a specific genotype. In case the trait of interest is not directly linked to a known genotype, or in case the linkage is complex, selection may be based on a phenotypic assay, for instance a bioassay.

The biotic stress resistance trait or pest resistance trait may be, but is not limited to, whitefly resistance, *phytophthora* resistance, leaf miner resistance (*Tuta absoluta*), spider mite resistance, greenhouse whitefly resistance, potato/tomato aphid resistance, thrips resistance, powdery mildew resistance, *Cladosporium* resistance, *Botrytis cinerea* resistance, bacterial resistance or any combination thereof. Optionally, the whitefly resistance, *Tuta absoluta*, thrips and aphid resistance are traits that are derived from a *Solanum pennellii* species. Optionally, the *phytophthora* resistance, *Cladosporium* resistance and/or bacterial resistance are traits that are derived from a *Solanum pimpinellifolium* species. Optionally, the powdery mildew resistance, *Botrytis cinerea* resistance and *phytophthora* resistance are traits that are derived from a *Solanum habrochaites* species. "Derived from" is to be understood here as meaning that the trait can be introduced in the first plant as defined herein by using the indicated wild species as first parent plant, optionally by crossing, and optionally further inbreeding, said first parent plant with a second parent plant being a *Solanum lycopersicum* variety or cultivar.

Suitable bioassays for detecting and selecting for such resistances are based on greenhouse/field trials wherein plants can be challenged with a pest, such as the arthropod, fungal, bacterial, oomycete and/or viral pest indicated above, wherein said plant is subsequently and reliably scored for resistance. In case of whitefly resistance, criteria for resistance may include the number of adults present on the plant, or the number of eggs laid, or the number of eggs that develop into adults, or a combination of these criteria. In case of leaf miner (*Tuta absoluta*), criteria for resistance may include the number of leaf miners present on the plant, number of eggs deposited, leaf surface eaten and/or damaged. In case of powdery mildew, criteria for resistance may include the number and/or size of infection spots present on the plant, or number of conidia (spores).

A suitable bioassay for detecting *Bemisia tabaci* (whitefly) resistance is described in WO2012/165961, which is incorporated herein by reference. In brief, plants to be tested for *B. tabaci* resistance and a control plants receive 4 clip cages, each of which contains 20 adult *B. tabaci* (preferably biotype Q) and reared continuously on cucumber under laboratory conditions (see Bleeker et al., 2009-Plant Physiol.). After 5 days, the total number and percentage of dead adults and total number of eggs (combined abaxial and adaxial side of leaves) is determined.

A suitable (phenotypic) bio-assay for detecting *Trialeurodes vaporariorum* (greenhouse whitefly) resistance is also described in WO2012/165961, which is incorporated herein by reference. In brief, *Trialeurodes vaporariorum* (order: Hemiptera) are reared on tomato (*S. lycopersicum*). A choice assay is performed for 24 hours. Adults were released in a cage with the plant to be tested and a control plant. Subsequently, adult settling preference was determined on leaves of the plant.

A suitable bioassay to detect *Macrosiphum euphorbiae* (potato/tomato aphid) resistance is also described in WO2012/165961, which is incorporated herein by reference. In brief, *Macrosiphum euphorbiae* (order: Hemiptera) are reared on tomato (*S. lycopersicum*). A no-choice assay is performed for 48 hours. One adult aphid is placed in a clip-cage on the plant to be tested and a control plant. Subsequently, aphid performance (survival and number of offspring) is determined.

A suitable bioassay to detect *Tuta absoluta* resistance is also described in WO2012/165961, which is incorporated herein by reference. In brief, *Tuta absoluta* (order: Lepidoptera) are reared on tomato (*S. lycopersicum*). A no-choice assay is performed for 7 days. 5 adults were allowed to oviposit their eggs on the plant to be tested and a control plant. After 7 days, *Tuta absoluta* oviposition (number of eggs deposited) is determined on the abaxial and adaxial side of each plant genotype.

A suitable bioassay to detect spider mites (*Tetranychus urticae* and/or *Tetranychus evansi*) is also described in WO2012/165961, which is incorporated herein by reference. Spider mites, like insects, belong to the arthropods but are a different class of organisms. In brief, the arthropod species are reared on common garden bean. A 4-day no-choice assay is performed with synchronized populations of *T. urticae* and/or *T. evansi*. Mites are place on leaf discs of the plant to be tested and a control plant. Subsequently, mite survival and fecundity (number of eggs/mite) is assessed.

Pest resistance may also, or in combination with the foregoing, be assessed by increased production of toxic and/or repellent molecules present in or on epidermal cells (e.g. terpenoids, terpenoid derivatives, methylketones and acylsugars), increased number of trichomes and/or increased amount of wax.

Abiotic stress resistance may be drought resistance, which is to be understood as having improved drought resistance as compared to a control plant not having drought resistance. A plant having improved drought resistance refers to plants which, when provided with improved drought resistance, when subjected to drought or drought stress do not show effects or show alleviated effects as observed in plants not provided with improved drought resistance. A normal plant has some level of drought resistance. It can easily be determined whether a plant has improved drought resistant by comparing a control plant with a plant provided with improved drought resistance under controlled conditions chosen such that in the control plants signs of drought can be observed after a certain period, i.e. when the plants are subjected to drought or drought stress. The plants with improved drought resistance will show less and/or reduced signs of having been subjected to drought, such as wilting, as compared to the control plants. The skilled person knows how to select suitable conditions such as for example the controlled conditions in the examples. When a plant has "improved drought resistance", it is capable of sustaining normal growth and/or normal development when being subjected to drought or drought stress would otherwise have resulted in reduced growth and/or reduced development of normal (control) plants. Hence, "improved drought resistance" can be determined by comparing plants, whereby the plant most capable of sustaining (normal) growth under drought stress is a plant with "improved drought resistant" plant. The skilled person is well aware how to select appropriate conditions to determine drought resistance of a plant and how to measure signs of droughts, such as described in for example manuals provided by the IRRI, Breeding rice for drought prone environments, Fischer et al., 2003, and by the CIMMYT, Breeding for drought and nitrogen stress tolerance in maize: from theory to practice, Banzinger et al, 2000. Examples of methods determining improved drought resistance in plants are provided in Snow and Tingey, 1985, Plant Physiol., 77, 602-7 and Harb et al., Analysis of drought stress in *Arabidopsis*, AOP 2010, Plant Physiology Review, and as described in the example section below. Increased drought resistance may also or in combination with the foregoing, be assessed by the increase amount of trichomes and/or decreased amount of stomata as compared to a control plant.

A germination property may be, but is not limited to, germination capacity, peak value time, uniformity of germination, germination rate, seed density and/or seed vigour. Germination properties are assessed on the seed produced by the plant of interest. More in particular, in case a property of seed germination is assessed for the chimera plant of the invention, said property is to be assessed for seed produced by said chimera plant after pollination of said plant. Improved germination is to be understood herein as at least one improved germination property of said seed obtained from the chimera plant as compared to seed obtained from a non-chimera control plant when pollinated with similar pollen (i.e. pollen from the same plant and having the same genotype), wherein the seed embryo of the seed of said chimera plant has the same genotype of the seed obtained from said control plant. In a preferred embodiment, germination properties of seed obtained from the chimera plant of the invention after pollination with pollen from the first parent plant as defined herein, is compared to seed obtained from the second plant as defined herein after pollination with pollen from said first parent plant.

Figure 11:
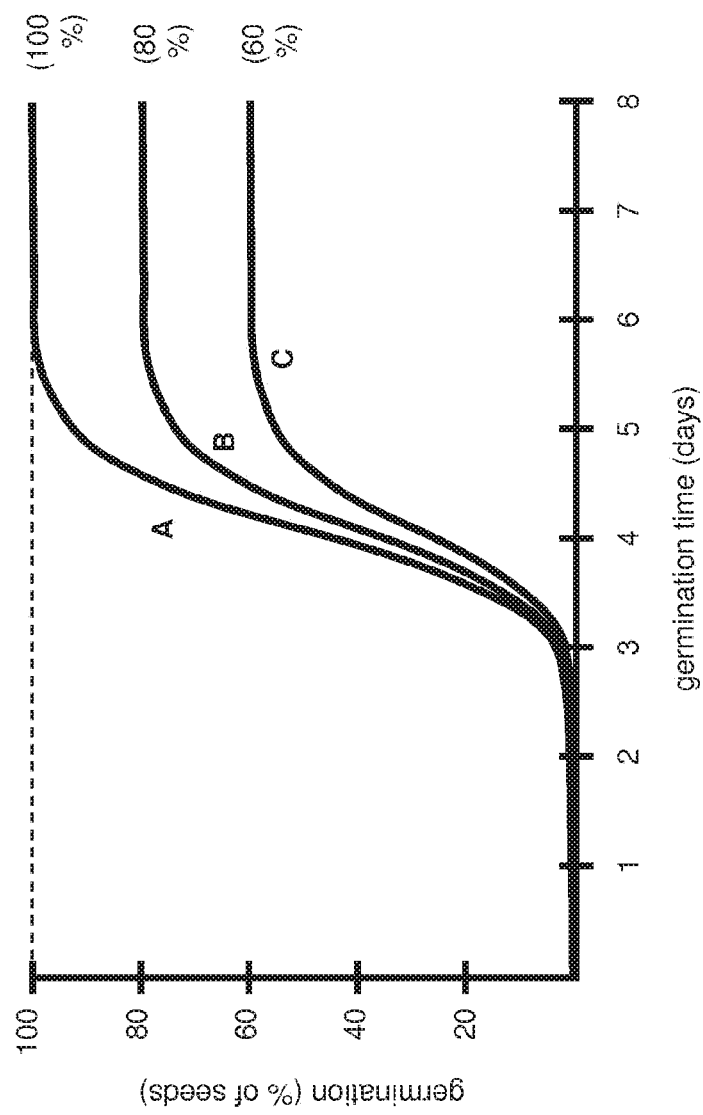
FIG. 11: Illustration of the development of the percentage of germinated seeds over time of plant lines with different germination capacity. Germination capacity is the number of germinated seeds expressed as a percentage of the total number of planted seeds in a given period of time. The period of time taken is long enough to make sure that the number of germinated seeds is levelling off in time, and reaches a plateau phase. This period of time for instance is 3 times the peak value time. This plateau phase may be 100%, when all seeds have germinated, or it may be a lower percentage, in case some seeds do not germinate at all. In the figure, line B is the control line with 80% germination capacity. Line A is an example of a line with improved germination capacity (100%), and line C an example of inferior germination capacity.

Germination capacity is to be understood as the percentage of sown or planted or otherwise distributed seeds that germinates, i.e. shows the emergence of the radicle, within a fixed period of time appropriate for the given plant species. Thus, germination capacity can be calculated as the number of seeds germinated divided by the total number of seeds sown or planted or otherwise distributed, recalculated as a percentage, within a given period of time. Seed germination properties may, for example be determined after sorting and selection procedures such as usual in agriculture and horticulture, and aimed at the specific plant species. Seeds may for example be separated by liquid density separation, or by X-ray sorting (for example as may be used for tomato seeds). The seeds may also be primed first. It is known to the skilled person how long the fixed period of time appropriate for a given plant species is. This period of time may for instance be 2, 3, 4 or 5 times the peak value time. Preferably it is 3 times the peak value time. It is known to the skilled person also that this period of time may vary according to environmental conditions. It is preferred that these conditions are optimal conditions for seed germination. The period of time is chosen thus long that variation in germination rate or germination uniformity does not influence the calculation of the germination capacity. The time period is appropriate if the skilled person can reasonably expect the majority of the seeds that are capable of germinating, to actually germinate within this time period. FIG. 11 illustrates the development of the percentage of germinated seeds over time of plant lines with different germination capacity. The period of time taken is long enough to make sure that the number of germinated seeds is levelling off in time, and reaches a plateau phase. This plateau phase may be 100%, when all seeds have germinated, or it may be a lower percentage, in case some seeds do not germinate at all. With germinating capacity is meant for instance 60%, 65%, 70%, 75%, 80%, 85%, 90% or 95%, depending on the plant species. Thus, an 85% germination capacity implies that 85% of the sown or planted or otherwise distributed seeds germinates, i.e. shows the emergence of a radicle, within a time period appropriate for the given plant species, for instance, but not limited to 3 times the peak value time. A higher germination capacity means that more seeds show emerged radicles. Examples of the fixed period of time appropriate for a given plant species in order to establish germination capacity under optimal environmental conditions are for instance, but not restricted to, about 5 days for *Arabidopsis*, about 7 days for barley, about 7 days for *Hypericum*, about 7 days for *Nicotiana*, about 7 days for tomato, about 28 days for buttercup, and about 30 days for *Impatiens*.

Figure 12:
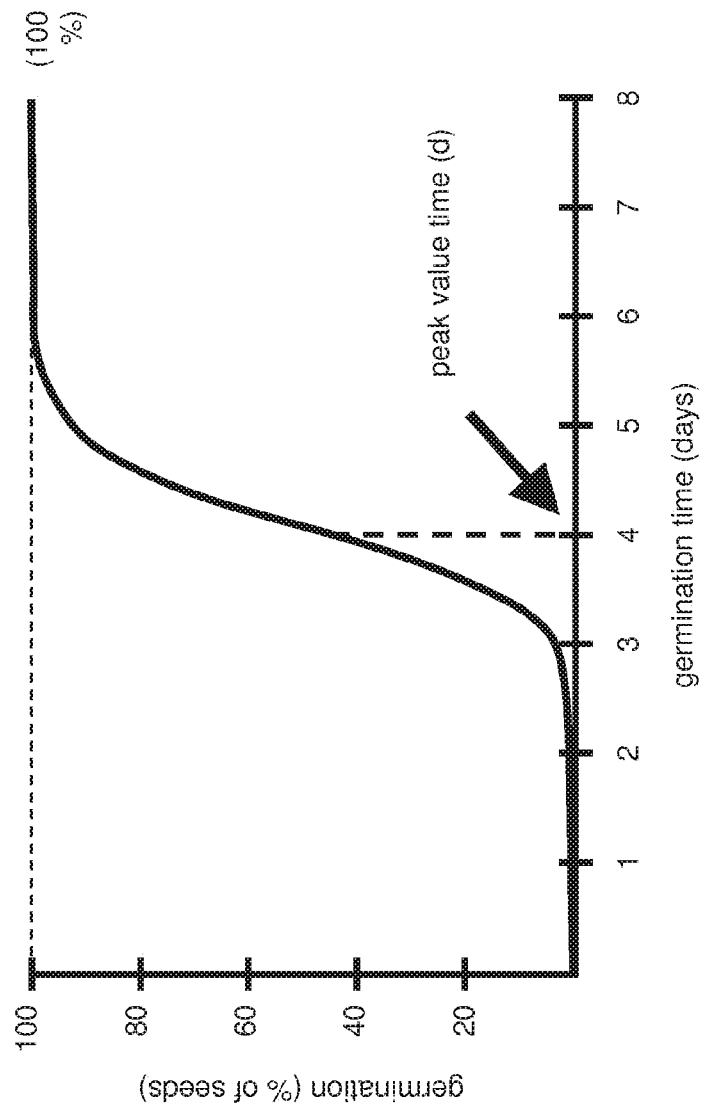
FIG. 12: Figure to illustrate the concept of peak value time. The peak value time is the point in time at which the tangent of the germination curve is steepest, i.e. at which the increase of germinating seeds per unit time is highest. Peak value time, being a time point related to the dynamics of the germination, can be used to define the time period needed to assess the germination capacity, e.g. a time period equal to 2, 3, 4 or 5 times, preferably 3 times the time span from seed planting to peak value time.

The peak value time is to be understood herein as the period of time after sowing, planting or otherwise distributing seeds in order for them to germinate, possibly after sorting and selection of the seeds, or for example after priming and/or stratification of the seeds, on which the highest tangent is reached on the curve in which percentage of germinated seeds is plotted on the y-axis, and time on the x-axis. FIG. 12 illustrates the concept of peak value time. Thus the peak value time is determined as the period of time required to reach the moment on which the increase in the number of germinating seeds per unit of time is the highest. The peak value time can be used to assist in calculating germination capacity or germination rate, for instance by fixing a time period of 2, 3, 4 or 5 times the peak value time, preferably 3 times the peak value time.

Uniformity of seed germination or germination uniformity is to be understood as the time (T) required to reach a fixed percentage of germinated seeds (X). This fixed percentage maybe 50% (T50), 75% (T75), 80% (T80), 90% (T90), 95% (T95), 99% (T99) or any percentage appropriate for a particular seed batch. The shorter this time, the higher the uniformity. It is known to the skilled person that uniformity of seed germination may vary according to environmental conditions. It is preferred that these conditions are optimal conditions for seed germination. Uniformity of seed germination is measured in such a way that it is in principle, but not necessarily, independent of germination capacity or germination rate.

Germination rate is defined as the weighted sum of total germinated seeds per day. In formula form: rate=(number of germinated seeds on day 1, divided by 1)+(number of germinated seeds on day 2, divided by 2)+ . . . +(number of germinated seeds on day Z, divided by Z) wherein Z is the last day of measurement. This measure is the same as the Germination Index (GI) defined by the American Association of Seed Analysts (AOSA) (AOSA., 1983. Seed vigor testing handbook. Contribution No. 32 to handbook on seed testing. Association of Official Seed Analysts). The germination rate is determined over a time period that is appropriate for the given plant species, and is the time period in which the skilled person can reasonably expect the majority of the seeds that are capable of germinating to actually germinate. The skilled person knows how to determine this time period. This period of time may for instance be 2, 3, 4 or 5 times the peak value time. Preferably it is 3 times the peak value time. It is known to the skilled person that germination rate may vary according to environmental conditions. It is preferred that these conditions are optimal conditions for seed germination. However, improved quality of a seed batch may also be assessed as a germination rate that is enhanced under suboptimal conditions, which may be prevalent in agronomic or horticultural practice.

Seed density relates to the specific weight of a seed and can be determined for instance by liquid density separation of seed, for instance in sucrose gradients.

Seed vigour means the ability of the seedling emerging from the seed to survive and grow when planted. Thus, seeds have a higher vigour, if under similar conditions a higher percentage of seedlings survives, and grows into seedlings or plantlets with emerged first true leaves, first by expanding the cotyledons, then by enlarging the shoot, and finally by producing the first true leaves. If under the same conditions a higher percentage of seedlings or plantlets with the first true leaves emerged can be observed within a certain time period which depends on the plant species, the seed vigour is considered higher. Seed vigour is also considered higher if the total biomass (fresh weight and/or dry weight) of the seedlings is larger after a fixed time period after sowing. Thus, seedling fresh weight is among other things a measure of seed vigour.

The ability to accept pollen that are produced by a particular plant, preferably the plant itself, i.e. pollen from the periclinal chimera plant to be produced can be assessed by pollinating the F1-hybrid or inbred first (parent) plant to be tested with pollen from the second plant which provides for the L2-shoot meristem layer of the periclinal chimera plant. Pollen acceptance is scored as positive when such pollinations results in the formation of fruit and seed.

In a particular embodiment, an L1 localized trait of interest is the ability to accept pollen that are produced by the first parent plant as defined herein. This trait is in particular of interest in combination with the trait of improved germination property of seed produced after pollination with pollen of said first parent plant. In particular, if said first parent plant is a wild species and the second plant that provides the L2 and L3 layer of the chimera plant of the invention is a cutlivar, hybrid seed can be produced by the chimera plant that shows improved germination properties as compared to hybrid seed produced with a non-chimera control plant (i.e. the second plant) after pollination with pollen of said first parent plant. In an even further preferred embodiment, said combination of L1-localized traits of interest further comprises the trait of a biotic or abiotic stress resistance.

The invention also provides for a periclinal chimera obtainable by any of the methods defined herein. Preferably, the resulting periclinal chimera plant is a commercially relevant plant that is characterized in that it comprises the (first, second and optionally further) trait of interest in the L1-shoot meristem layer. The invention further provides for a periclinal chimera that is vegetatively derived from the periclinal chimera obtained or obtainable by any of the methods defined herein.

Preferably, the first plant comprises a first and a second L1-localized trait of interest. It is thus no requirement for the first plant as defined herein to be a commercially relevant plant as a whole. Preferably the L1-shoot meristem layer of said first plant is commercially relevant, meaning that if the L1-shoot meristem layer of said plant is combined with the L2 and L3-shoot meristem layers of a second, commercially relevant, plant in order to produce a periclinal chimera plant, such periclinal chimera plant is commercially relevant.

A "first plant", "second plant", "first parent plant", "second parent plant" "F1-hybrid" and "inbred plant" as used herein may be replaced herein by "a plant having the genome of the first plant", "a plant having the genome of the second plant", "a plant having the genome of the first parent plant", "a plant having the genome of the second parent plant", "a plant having the genome of the F1-hybrid" and "a plant having the genome of the inbred plant", respectively.

A periclinal chimera plant may be made by a method suitable in the art. For instance, a periclinal chimera may be made by grafting seedlings of the plant or plant variety that will provide for the L1-shoot meristem layer (first plant as defined herein above) and the plant or plant variety that will provide for the L2 and L3 shoot meristem layer (second plant as defined herein above), consisting of the steps of (1)

transversely cutting and then adjoining and reunion of their hypocotyls, (2) cutting transversely through the graft junction, and (3) letting callus develop and adventitious shoots regenerate from the site of the graft union and (4) selecting chimeras among the regenerated plants. Techniques for steps 1-4 are known to a person skilled in the art. Generally, using grafting and regeneration, the frequency with which periclinal chimeras emerge among the adventitious shoots will be ~0.2%-10%. Therefore, preferably a large number of seedlings of first plant and second plant, and many independent adventitious shoots are generated. Each of these adventitious shoots may be grown into plantlets of around 5 cm in length, carrying a few leaves. From these plantlets, the apical shoot tip may be removed to allow axillary shoots to emerge from the leaf axils. Periclinal chimeras may be identified among these axillary shoots, by the use of genetic markers that distinguish the constituent first plant and second plant. These markers may be phenotypic, for example a distinctive leaf colour, or any morphological or biochemical difference, such as fruit shape. These markers may also be genotypic, such as a DNA or RNA sequence polymorphism between the plant providing the L1 shoot meristem layer and the plant providing the L2 and L3 shoot meristem layer. Phenotypic and/or genotypic markers may be detected by an appropriate detection method and applied to all axillary shoots from all adventitious shoots regenerated from all individual grafted plant-pairs. Periclinal chimeras can be recognized as having markers of both the first plant and the second plant combined in a single plant, as a result of adventitious shoot regeneration from graft junctions and not of sexual hybridization. Such chimeras stably retain these markers during further growth of the plant, including their axillary shoots, inflorescences, flowers, and all other aerial parts of the plants that arise from natural growth and development from the periclinal chimeric shoot apical meristem. Periclinal chimeras of the desired type, in terms of the constitution of its stem cell layers L(1,2,3), are identified by observing the presence of the markers in specific tissues, e.g. in the epidermis (L1), the vasculature (L3), the pollen grains (L2), or any other tissue known to mainly derive from these layers.

For instance, the first plant for producing a periclinal chimera plant comprising both a first and a second trait of interest, may be grafted as rootstocks or as scions to a second plant as defined above, followed by graft healing for 10 days. Graft junctions may then be transversely cut, upon which callus growth and shoot regeneration occurs spontaneously. Among regenerated shoots, periclinal chimeras may be selected visually, for instance by using the phenotypic marker xa (Szymkowiak, E. J., and Sussex, I. M. (1992), The internal meristem layer (L3) determines floral meristem size and carpel number in tomato periclinal chimeras, Plant Cell 4, pp. 1089-1100) and trichome density. The semi-dominant marker xa in heterozygous condition, causes yellow leaves when present in L2 and/or L3. For instance, in case the first plant (i.e. the plant providing the L1 shoot meristem layer) comprises the xa marker, while this marker is not present in the second plant as defined herein (i.e. plant providing the L2 and L3 shoot meristem layer), and the first plant has a phenotype of high trichome density which is not present in the second plant, the chimera of the desired type may be recognized by having green leaves (L2 and L3 of the second plant), plus a high trichome density (L1 of the inbred line). Further, the L1 layer identity may be determined by scoring the presence/absence in epidermal cells of a SNP marker that distinguished the genotype of the first plant for the genotype of the second plant.

The present invention also provides for a periclinal chimera plant obtained or obtainable by the method as defined above and/or any plant vegetatively derived from said periclinal chimera plant. Such periclinal plant may be recognized in that the genotype of the L1-shoot meristem layer differs from the genotype of the L2- and L3-shoot meristem layer and/or in that the plant comprises the (first, second and optionally further) trait of interest as defined herein above. The invention further provides for a periclinal chimera plant that has been fertilized, i.e. comprises a seed embryo. Preferably, the periclinal chimera plant has been fertilized by the pollen of a plant having the genotype of the first plant or second plant. The plant may be a rootstock variety.

The periclinal plant may further be recognized in that it preferably is a commercially relevant plant. The periclinal chimera plant (or plants vegetatively derived thereof) can be used for producing a plant product. Therefore, also provided is the use of said periclinal chimera plant (or plants vegetatively derived thereof) for producing a plant product. More in particular, provided is a method for producing a plant product from a periclinal chimera plant comprising a first and second trait of interest, wherein said method comprises the steps of:

A) providing a periclinal chimera plant comprising the first and second trait as defined above and/or obtainable by the method for producing a periclinal chimera plant as defined above;
B) growing the periclinal chimera plant of step A);
C) deriving a plant product from the plant grown in step B); and,
D) optionally, further processing the plant product obtained in step C).

Also provided is a plant product thus obtained. Said plant product may be selected from, but is not limited to, fruit, plant organ, plant parts (such as leave, root, root tip, stem, flower, flower bud, anthers, seed, grain, pollen, ovules), but may also be products that cannot give rise to a plant itself (i.e. non-propagating), such as plant fats, plant oils, plant starch, and plant protein fractions. The plant product does not need to possess the property of photosynthesis. Said processing in step D) may be selected from, but is not limited to, crushed, milled or still intact, mixed with other materials, dried, frozen and any combination thereof. The plant product may be recognized by the presence of the genotype of the L1-shoot meristem layer, and of the L2- and L3-shoot meristem-layer.

In an embodiment of the method or use of the invention, the first plant and the L1-shoot meristem layer of the periclinal chimera plant have the genotype of a first generation F1 hybrid of an *Solanum lycopersicum* inbred line with *Solanum* pennellii; the second plant and the L2-shoot and L3-shoot meristem layer of the periclinal chimera plant have the genotype of an inbred line of *Solanum lycopersicum*. All other variables may be as defined herein above. Preferably, within this embodiment, the first plant and L1-shoot meristem layer of the periclinal chimera plant have the genotype of a first generation F1 hybrid of the *Solanum lycopersicum* inbred line Ailsa Craig with *Solanum pennellii* line LA716. Preferably, the second plant and the L2-shoot and L3-shoot meristem layer of the periclinal chimera plant have the genotype of an inbred line of *Solanum lycopersicum* cv. MoneyMaker.

In an embodiment of the method or use of the invention, the first plant and the L1-shoot meristem layer of the periclinal chimera plant have the genotype of a first generation F1 hybrid of a *S. lycopersicum* inbred line and a cherry-type *S. lycopersicum* inbred line; the second plant and the L2-shoot and L3-shoot meristem layer of the periclinal chimera have the genotype of an inbred line of a beef variety of *Solanum lycopersicum*. All other variables may be as defined herein above. Preferably, within this embodiment the first plant and L1-shoot meristem layer of the periclinal chimera plant have the genotype of a first generation F1 hybrid of the *Solanum lycopersicum* inbred line Ailsa Craig with the cherry-type *S. lycopersicum* inbred line.

In an embodiment of the method or use of the invention, the first plant and the L1-shoot meristem layer of the periclinal chimera plant have the genotype of a first generation F1 hybrid of an *Solanum lycopersicum* inbred line with *S. habrochaites*; the second plant and the L2-shoot and L3-shoot meristem layer of the periclinal chimera have the genotype of an inbred line of *Solanum lycopersicum*. All other variables may be as defined herein above. Preferably, within this embodiment the second plant and the L2-shoot and L3-shoot meristem layer of the periclinal chimera have the genotype of a *Solanum lycopersicum* cv. MoneyMaker and the first plant and L1-shoot meristem layer of the periclinal chimera plant have the genotype of a first generation F1 hybrid of the *Solanum lycopersicum* inbred line Ailsa Craig with *Solanum habrochaites* accession PI127826.

In an embodiment of the method or use of the invention, the first plant and the L1-shoot meristem layer of the periclinal chimera plant have the genotype of a first generation F1 hybrid of an *Solanum lycopersicum* inbred line with *S. pennellii* which was subsequently backcrossed as a male to an *S. lycopersicum* female, to produce a BC1 population; the second plant and the L2-shoot and L3-shoot meristem layer of the periclinal chimera have the genotype of an inbred line of *Solanum lycopersicum*. All other variables may be as defined herein above. Preferably, the first plant and L1-shoot meristem layer of the periclinal chimera plant have the genotype of a first generation F1 hybrid of a *Solanum lycopersicum* inbred line LA3579 with *S. pennellii* which was subsequently backcrossed as a male to an *S. lycopersicum* LA3579 female, to produce a BC1 population. Preferably, This BC1 population was selected for the simultaneous phenotypic expression of the whitefly resistance, cross compatibility as a female with pollen from any paternal accession and xa marker of LA3579.

In an embodiment of the method or use of the invention, the first plant and the L1-shoot meristem layer of the periclinal chimera plant have the genotype of a first generation F1 hybrid of an *Solanum lycopersicum* inbred line with *S. pimpinellifolium*; the second plant and the L2-shoot and L3-shoot meristem layer of the periclinal chimera have the genotype of an inbred line of *Solanum lycopersicum*. All other variables may be as defined herein above. Preferably, within this embodiment the first plant and L1-shoot meristem layer of the periclinal chimera plant have the genotype of a first generation F1 hybrid of the *Solanum lycopersicum* inbred line Ailsa Craig with *S. pimpinellifolium* accession CGN1552937 and the second plant and the L2-shoot and L3-shoot meristem layer of the periclinal chimera have the genotype of the *Solanum lycopersicum* cv. MoneyMaker.

Within this disclosure, a *Solanum lycopersicum* plant variety Ailsa Craig can have accession number LA3579 and *Solanum lycopersicum* plant variety MoneyMaker can have e.g. accession LA2706.

The invention is further explained in the following examples. These examples do not limit the scope of the invention, but merely serve to clarify the invention.

Example 1

Tomato plants resistant to whiteflies (*Bemisia tabaci*, biotypeQ) were made as follows. An F1 hybrid was made between a whitefly resistant accession (*Solanum pennellii* LA716) and a whitefly susceptible accession (*Solanum lycopersicum* LA3579), the latter containing the semi-dominant xa phenotypic marker, a marketable red fruit color, and cross compatibility as a female with pollen from any paternal accession, line or hybrid of *S. lycopersicum*. An F1-hybrid was selected for the simultaneous phenotypic expression of the whitefly resistance and the xa marker of LA3579.

The resulting F1 hybrid was grafted as scions to a commercially relevant susceptible inbred variety of *S. lycopersicum*, herein further denominated as "susceptible control", followed by graft healing for 7 days. Graft junctions were then transversely cut, upon which callus growth and shoot regeneration occurred spontaneously. Among regenerated shoots, periclinal chimeras were selected visually, using the phenotypic marker xa plus high trichome density carried by hybrid scions. The semi-dominant marker xa, in heterozygous condition, causes yellow leaves when present in L2 and/or L3. The chimera of the desired type was recognized by having green leaves (L2 and L3 of the cultivar), plus a high trichome density (L1 of hybrid). The chimera was very stable throughout development and during propagation from rooted cuttings of axillary shoots, as judged by the complete absence of spontaneous invasions of L1 cells into L2, which would have been seen as yellow sectors in leaves and stems.

The chimera(s) so produced were tested for whitefly resistance in a greenhouse trial under commercial Mediterranean growing conditions (El Ejido, Spain) with high pressure of *B. tabaci* and TYLCV (Tomato yellow leaf curl virus). Plants were reliably scored for resistance by counting the number of adults, eggs, nymphs and exuviae present on the plant and comparing this the resistant control (F1-hybrid) and susceptible control over a period of 2.5 months.

It was found that the resistant control (F1-hybrid) performed well over the entire length of the experiment (2.5 months). Limited numbers of whiteflies (adults and nymph stages) were detected on these plants and only mild TYLCV symptoms were observed in the apical part of the plant towards the end of the experiment. In contrast, susceptible plants were covered with whiteflies (all life stages) and showed TYLCV symptoms as early as Nov. 4, 2015. TYLCV symptoms quickly worsened and plants remained stunted (~50 cm) throughout the remainder of the experiment.

Interestingly, the tester plants, *S. lycopersicum* onto which the L1-shoot meristem layer of *S. pennellii*×*S. lycopersicum* was transferred, were almost free of whiteflies (all life stages; similar to the resistant control plants), grew strongly and developed only mild TYLCV symptoms towards the end of the experiment.

FIGS. 1-4 represent the average number of whitefly adults, eggs, nymphs and exuviae that were observed over time on these plants (A, B and C) in the heavily infested greenhouse. All data show significant differences when comparing A or C plants to the susceptible control (B).

In an independent repeat of this experiments, wherein 20 chimera plants containing at least 4 true leaves and produced as indicated above were tested for Bt-resistance using the clip-cage assay as defined herein, clear differences in Bt-mortality was found after 48 hours between susceptible control plants (*S. lycopersicum*), F1 donor plants and chimeric plants and as shown in Table 1. The whiteflies used in this clip-cage experiment, were 4 weeks old (egg-adult stage), obtained from a synchronized rearing on cotton plants and collected with an exhauster. The whiteflies were transferred from the tube into the clip-cage while numbed with $CO_2$ for 5 seconds (6 female whiteflies per clip-cage). After 48 hours, the clip-cages were reopened, whiteflies were recaptured and mortality was scored.

TABLE 1

Field number, number of plants (n), Mean dead whiteflies in percentage from total (%) and StdDev (%).

| Field number | Number (n) | Mean (%) | Std Dev (%) |
|---|---|---|---|
| S. lycoperiscum | 20 | 2.6 | 6.5 |
| Donor (F1 S. lyc × S. penn) | 18 | 9.5 | 12.1 |
| Chimeric plant | 20 | 54.6 | 34.0 |

In addition to the adult mortality, the number of pupa and exuviae was determined in these plants three weeks later. As shown in Table 2, whitefly development from egg to exuviae was significantly lower on the donor and chimeric plant compared to *S. lycopersicum*, indicating higher levels of resistance to whiteflies.

TABLE 2

Field number, number of plants (n), Mean number of offspring in pupal stage as percentage from total (%) and StdDev (%).

| Field number | Number (n) | Mean (%) | Std Dev (%) |
|---|---|---|---|
| S. lycoperiscum | 20 | 76.6 | 27.0 |
| Donor (F1 S. lyc × S. penn) | 18 | 24.9 | 14.5 |
| Chimeric plant | 20 | 9.6 | 8.7 |

Example 2

Tomato plants resistant to whiteflies (*Bemisia tabaci*, biotypeQ) is made as follows. An F1 hybrid was made between a whitefly resistant accession (*Solanum* pennellii LA716) and a susceptible accession (*Solanum lycopersicum* LA3579), the latter containing the semi-dominant xa phenotypic marker, a marketable red fruit colour, and cross compatibility as a female with pollen from any paternal accession, line or hybrid of *S. lycopersicum*. The resulting F1 hybrid was backcrossed as a male to an *S. lycopersicum* LA3579 female, to produce a BC1 population. This BC1 population was selected for the simultaneous phenotypic expression of the whitefly resistance, cross compatibility as a female with pollen from any paternal accession and xa marker of LA3579.

Selection for whitefly resistance was done as indicated in Example 1. In addition, selection included the ability of the plants to accept pollen of *S. lycopersicum*. The latter was done by pollinating the selected plants with pollen from a line or hybrid of *S. lycopersicum*. Pollen acceptance was scored as positive when such pollinations resulted in the formation of fruit and seed. Selected plants were subsequently inbred for three and four generations, respectively, to produce the BC1S3 and BC1S4 population. In each of these three and four generations, respectively, selection is carried out in the same way as described above, with the inclusion of the trait of marketable red fruit colour, resulting in a plant that is whitefly resistant, compatible with *S. lycopersicum* pollen, and carries red pigments in ripe fruit. Whitefly (Bt) mortality was tested using the clip-cage assay as defined herein, wherein Bt mortality was determined after 5 days. Moreover, the number of eggs deposited was counted. Whitefly (Bt) mortality was significantly increased in BC1S3 and BC1S4 plants (FIG. 14). More strikingly, very few eggs were observed on these plants (FIG. 15).

These BC1S3 and BC1S4 plant resistant to whiteflies selected and propagated as indicated above (line progeny or clone), herein further denominated as "BC1S3" and "BC1S4", are grafted as rootstocks or as scions to a commercially relevant inbred variety or F1 hybrid of *S. lycopersicum*, herein further denomited as "cultivar".

Periclinals are produced by first grafting BC1S3 or BC1S4 scions onto cultivar rootstocks, followed by graft healing for 7 days. Graft junctions are then transversely cut, upon which callus growth and shoot regeneration occurs spontaneously. Among regenerated shoots, periclinal chimeras are selected visually, using the phenotypic marker xa plus high trichome density carried by BC1S3 and BC1S4 scions. The semi-dominant marker xa, in heterozygous condition, causes yellow leaves when present in L2 and/or L3. The chimera of the desired type is recognized by having green leaves (L2 and L3 of the cultivar), plus a high trichome density (L1 of BC1S3 and BC1S4).

The chimera(s) so produced is tested for whitefly resistance by the methods described above, for pollen compatibility by self-fertilisation of the periclinal chimeric plants, and for the formation of red fruit. Subsequently, chimeras are propagated as clones by taking axillary shoots as rooted cuttings. Populations of such clones can be used for commercial tomato fruit production in manners that are common in the industry.

Example 3

The germination properties of tomato seeds from the interspecific F1 hybrid TP were improved. This F1 hybrid is produced by crossing a maternal inbred line TT of *S. lycopersicum* to a paternal line PP of *S. pennellii*.

A periclinal chimera was made of type {L3 (TT), L2 (TT), L1 (EP)}, wherein TT and EP denote diploidy (where T and E and P are haploid). TT is a standard inbred tomato (*S. lycopersicum*) variety. EP is a first generation F1 hybrid of *S. lycopersicum* inbred line EE (cv Ailsa Craig accession LA3579), and a *S. pennellii* line PP (accession LA716). Periclinals were produced by first grafting EP scions onto TT rootstocks, followed by graft healing for 10 days. Graft junctions were then transversely cut, upon which callus growth and shoot regeneration occurred spontaneously. Among regenerated shoots, periclinal chimeras were selected visually, using the phenotypic marker xa plus high trichome density carried by EP scions. The semi-dominant marker xa, in heterozygous condition, causes yellow leaves when present in L2 and/or L3. The chimera of the desired type was recognized by having green leaves (L2 and L3 of TT), plus a high trichome density (L1 of EP). The chimera was very stable throughout development and during propagation from rooted cuttings of axillary shoots, as judged by the complete absence of spontaneous invasions of L1 cells into L2, which would have been seen as yellow sectors in leaves and stems. The breeding behavior of the chimera was analyzed using segregation analyses of the xa marker. In 500 seedlings of the chimera, from a backcross to PP, we have not observed a single yellow seedling. These data showed that the chimera carried gametophytes exclusively from genotype T, and that the EP tissues only served a sporophytic role. Because the L1 layer is well known to give rise to the integuments of the ovule and later to the seed coat of the mature seed, the sporophytic role of EP in seed development of the chimera has been that of integuments and seed coat.

Interspecific TP F1-hybrid seeds were produced from the chimera, as well as from non-chimeric TT plants. To this end, 6 plants of each were grafted onto a rootstock of genotype TT, to equalize their root systems. They were cross fertilized with pollen from line PP to produce TP hybrid seed (F1). All plants were grown in a regular greenhouse in the period April-August. Crosses were made by emasculating flowers just before anthesis, followed by pollination 1-2 days later. Seeds were harvested from ripe fruits, soaked in 0.5% HCl for 1 hour, then thoroughly rinsed under tap water, dried on filter paper and stored at 10 degrees Celsius/10% relative humidity, until use.

We defined and measured 3 germination properties of the seeds:
(a) density
(b) germination rate
(c) germination capacity All measurements were taken in the following sequential way:

(a) Density

The density of a mature seed is a direct function of its physiological composition. It is mainly determined by the amount and the biochemical nature of metabolic compounds in endosperm and embryo, which occupy the space within the seed coat. Density (specific weight) was determined by liquid density separation in solutions of sucrose in water. ~500 seeds were sequentially passed through 0, 200 and 400 grams sucrose per liter water in a graduated cylinder. Seeds that sank in the lighter solution were collected and taken to the next. This resulted in 4 density fractions, from low to high: 0, 200, 400 and 400+. Fractions were thoroughly rinsed in tap water and dried for at least 72 hours on filter paper at room temperature. The number of seeds per fraction was counted, and the distribution over the density classes determined.

Figure 1:
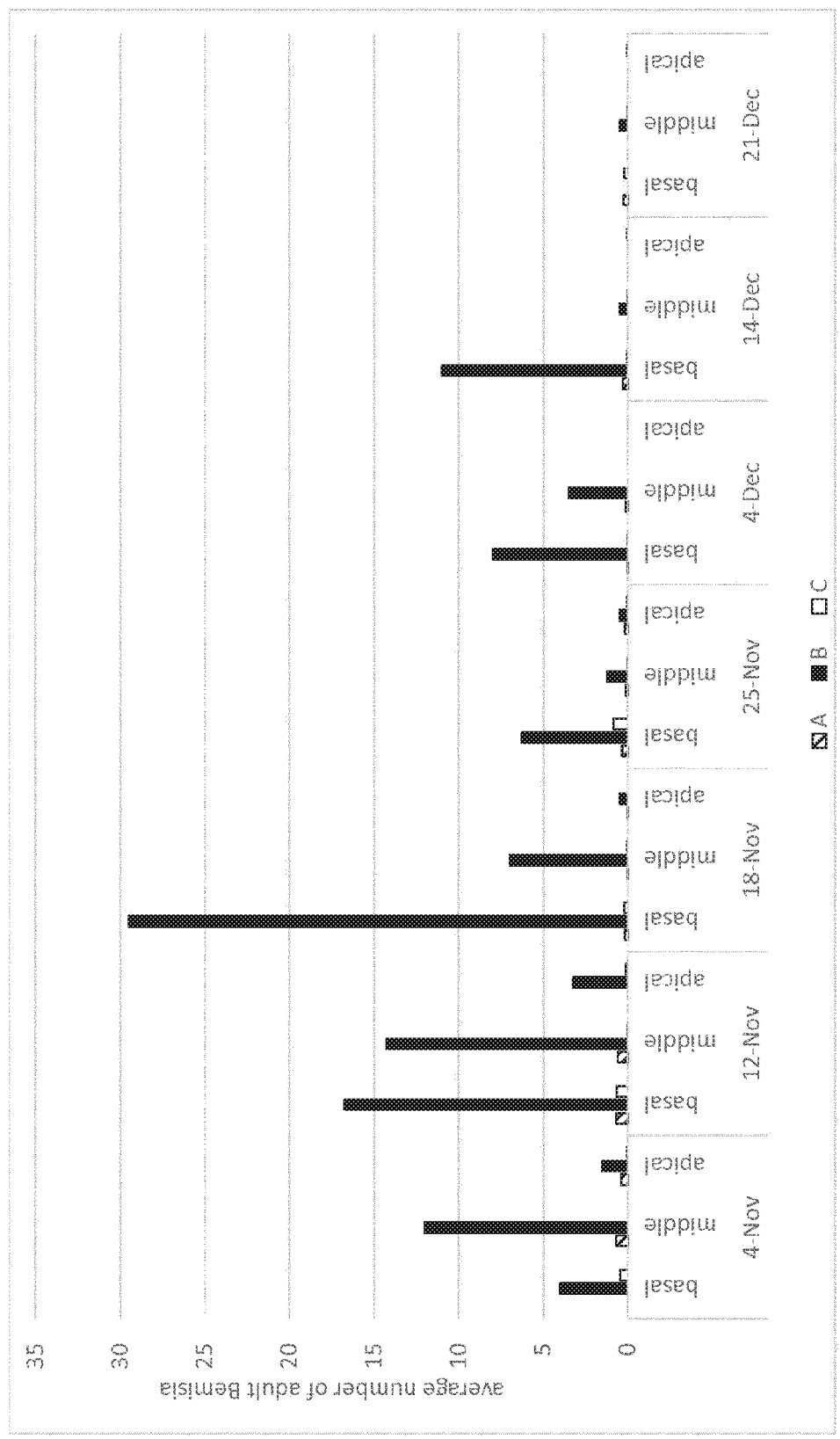
FIG. 1: Average number of adult *Bemisia Tabaci* on three plant genotypes. A: *S. lycopersicum* onto which the L1-shoot meristem layer of *S. pennellii×S. lycopersicum* was transferred (test plant; periclinal chimera having L2 and L3 of *S. lycopersicum* and L1 of F1 from cross of *S. pennellii×S. lycopersicum*); B: *S. lycopersicum* (susceptible control); C: *S. pennellii×S. lycopersicum* (F1; resistant control).
Figure 2:
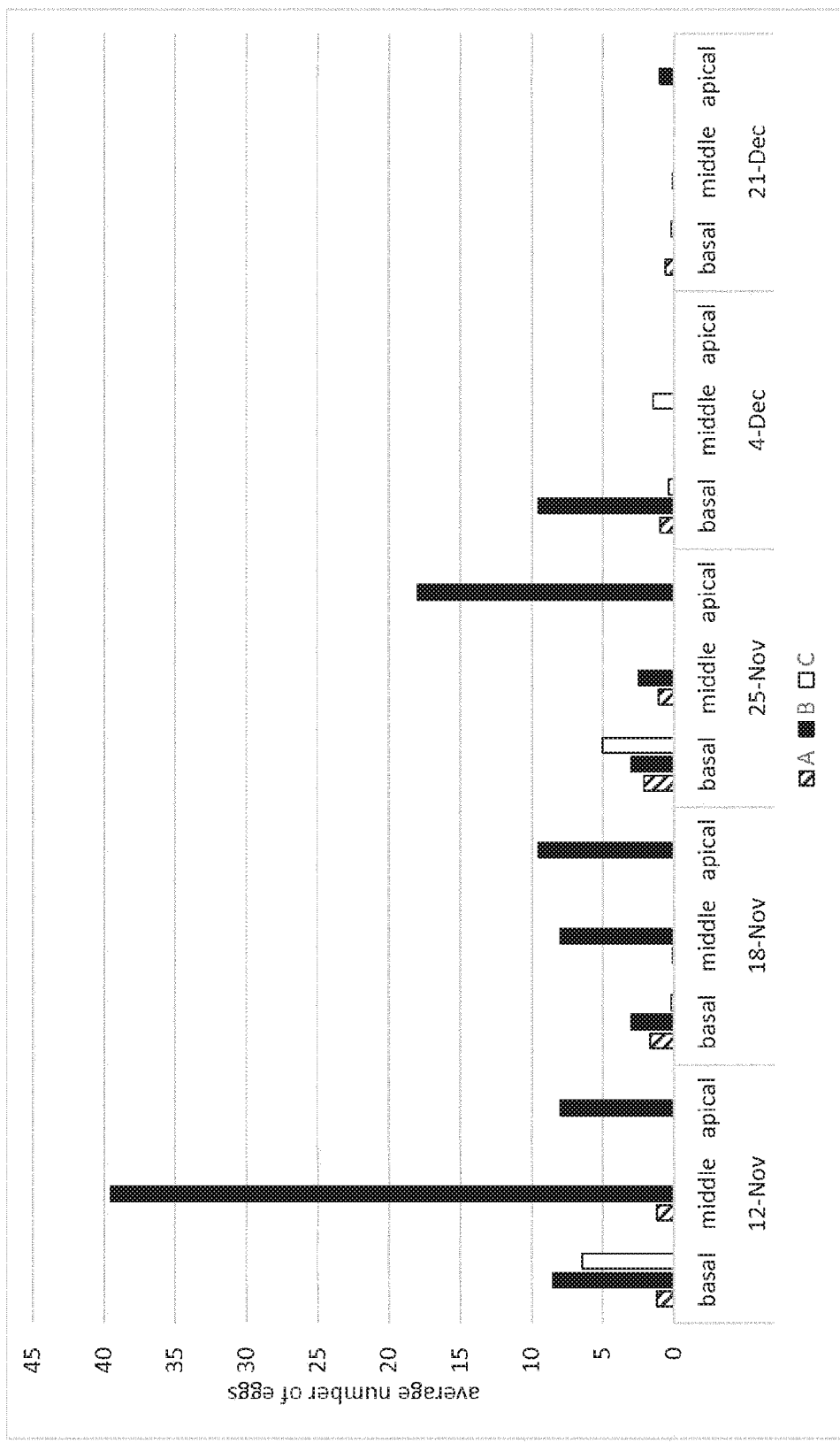
FIG. 2: Average number of *Bemisia Tabaci* eggs on three plant genotypes. A: *S. lycopersicum* onto which the L1-shoot meristem layer of *S. pennellii×S. lycopersicum* was transferred (test plant; periclinal chimera having L2 and L3 of *S. lycopersicum* and L1 of F1 from cross of *S. pennellii×S. lycopersicum*); B: *S. lycopersicum* (susceptible control); C: *S. pennellii×S. lycopersicum* (F1; resistant control).
Figure 3:
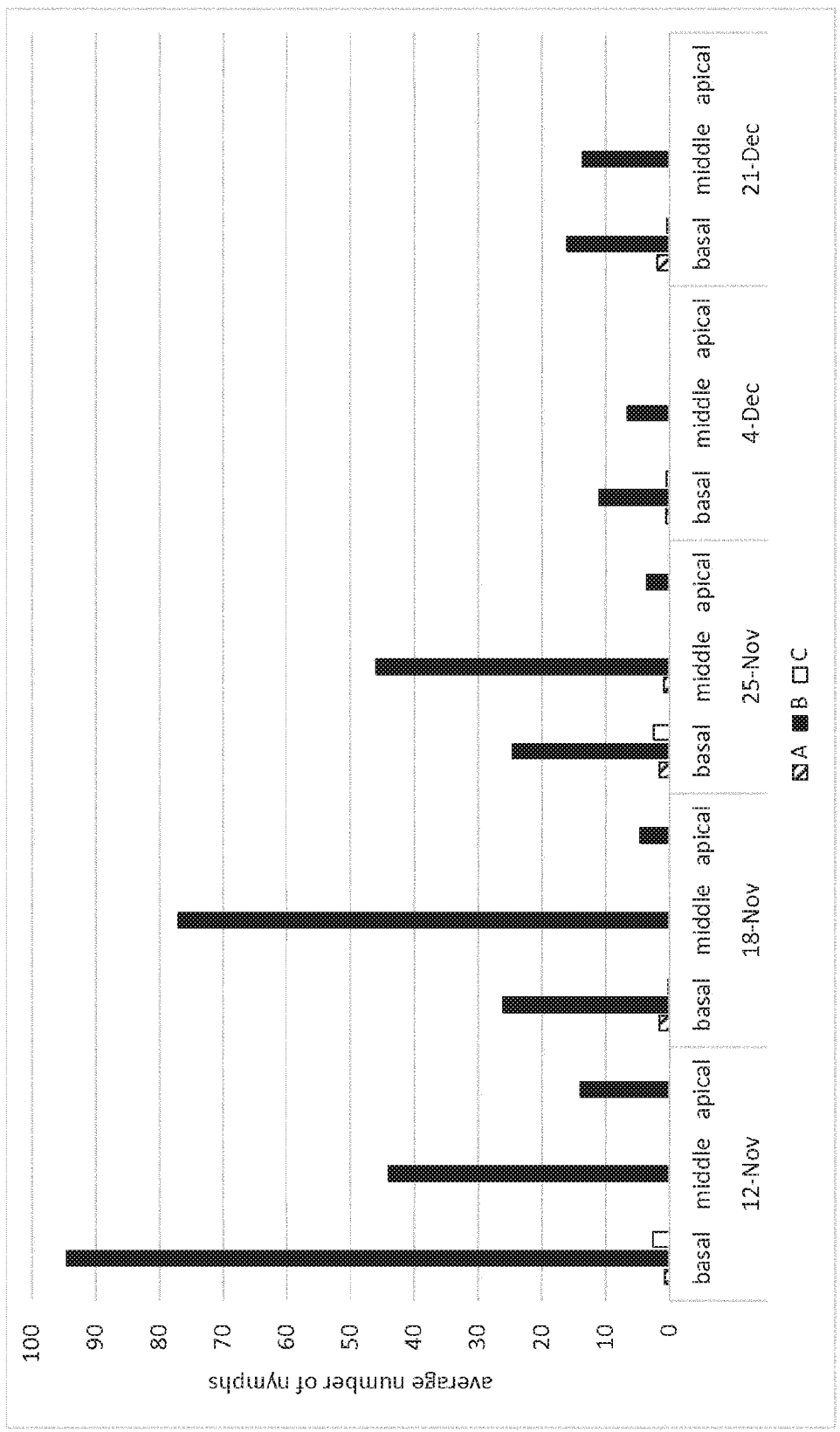
FIG. 3: Average number of *Bemisia Tabaci* nymphs on three plant genotypes. A: *S. lycopersicum* onto which the L1-shoot meristem layer of *S. pennellii×S. lycopersicum* was transferred (test plant; periclinal chimera having L2 and L3 of *S. lycopersicum* and L1 of F1 from cross of *S. pennellii×S. lycopersicum*); B: *S. lycopersicum* (susceptible control); C: *S. pennellii×S. lycopersicum* (F1; resistant control).
Figure 4:
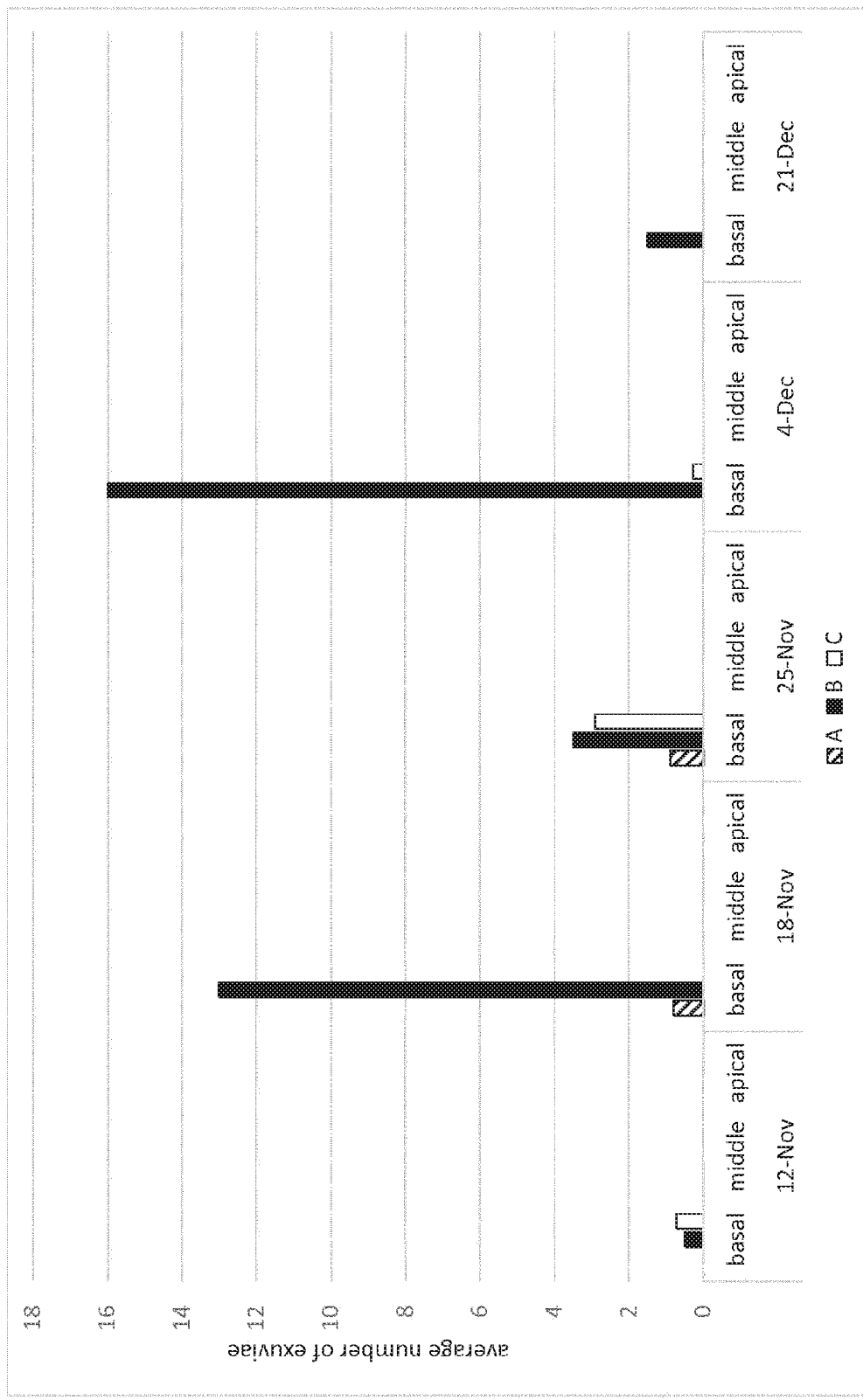
FIG. 4: Average number of *Bemisia Tabaci* exuviae on three plant genotypes. A: *S. lycopersicum* onto which the L1-shoot meristem layer of *S. pennellii×S. lycopersicum* was transferred (test plant; periclinal chimera having L2 and L3 of *S. lycopersicum* and L1 of F1 from cross of *S. pennellii×S. lycopersicum*); B: *S. lycopersicum* (susceptible control); C: *S. pennellii×S. lycopersicum* (F1; resistant control).
Figure 5:
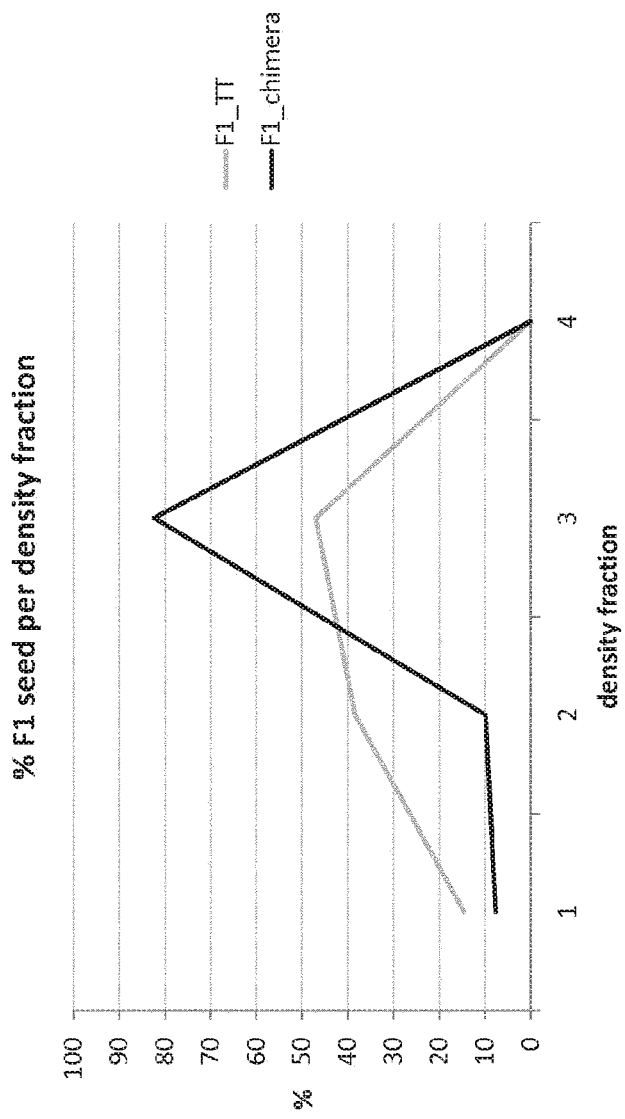
FIG. 5: Density distribution of seeds. At density class "3", the lines represent from top to bottom: F1_chimera (progeny of the cross-fertilization of the chimera with line PP) and F1_TT (progeny of the cross-fertilization of the non-chimeric plant TT with line PP).

As shown in FIG. 5, interspecific F1 seeds made from crosses of non-chimeric TT to PP had a density distribution very different from the chimera crossed to PP. In contrast to the chimeric cross, the non-chimeric cross had a high proportion of poorly filled, light seeds. Because the genotypes of embryo and endosperm in these two crosses are identical, it must be concluded that the difference in density distribution had been physiologically imparted onto the seeds by the EP sporophyte. A high proportion of poorly filled seeds is characteristic of the cross *S. lycopersicum*×*S. pennellii*, and is a manifestation of a mild interspecific crossing barrier between these species. The chimera significantly relaxed this barrier.

(b) Germination Rate

Germination rate was determined in vitro by sowing 100 seeds in a gridded array on moistened (tap water) filter paper in a sealed petridish, followed by incubation under 16/24 hours of white light in a climate chamber at 23 degrees Celsius. Germination was scored in 24 hour intervals as the visible emergence of a radicle, over a period of 7 days. The rate was then calculated according the formula: rate=(#1/1)+(#2/2)+ . . . +(#7/7), wherein #1 is the number of germinated seeds after 24 hours, #2 the number of germinated seeds after 48 hours, etc. The higher the rate number, the quicker the emergence of radicles. Tests were done with a 100-seed sample.

Figure 6:
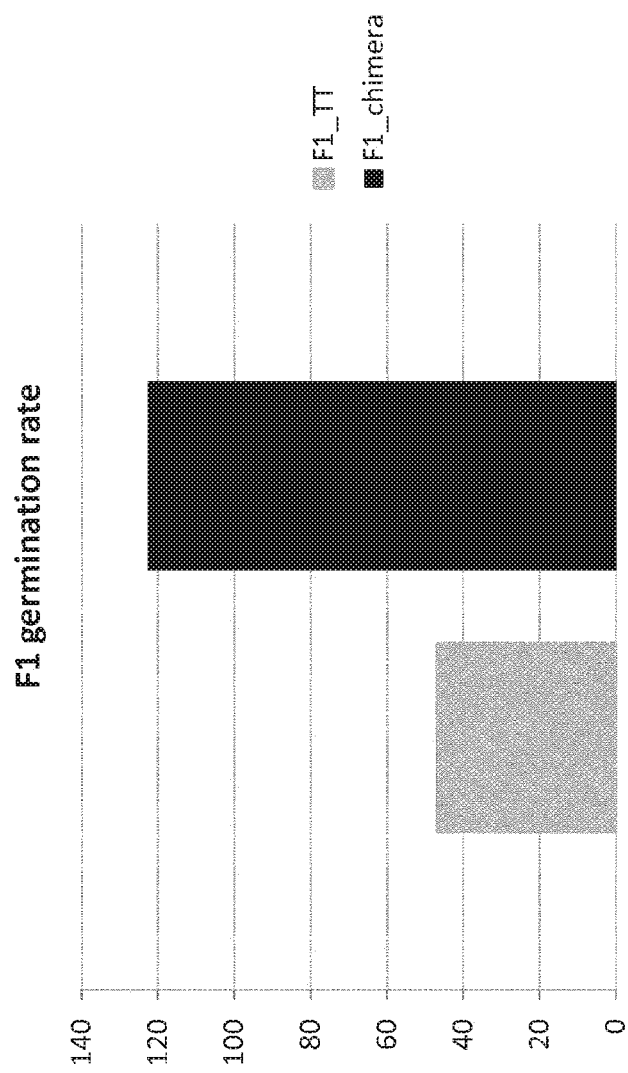
FIG. 6: Germination rate of seeds. Left column represents F1_TT (progeny of the cross-fertilization of the non-chimeric plant TT with line PP), right column represents F1_chimera (progeny of the cross-fertilization of the chimera with line PP).

FIG. 6 shows the results of in vitro germination rate tests of F1 seeds from the chimera and from TT control plants. Only raw seeds batches were sown, i.e. they were not density fractionated before sowing. From FIG. 6 it is clear that the chimera produced seed batches with a higher germination rate. Because embryos and endosperm from the chimera and from the TT control are genetically identical, it must be concluded that the germination rate difference had been conferred physiologically by sporophyte EP. Retarded seed germination is characteristic of the cross *S. lycopersicum*×*S. pennellii*, and is a manifestation of a mild interspecific crossing barrier between these species. The chimera significantly overcomes this barrier.

(c) Germination Capacity

Figure 7:
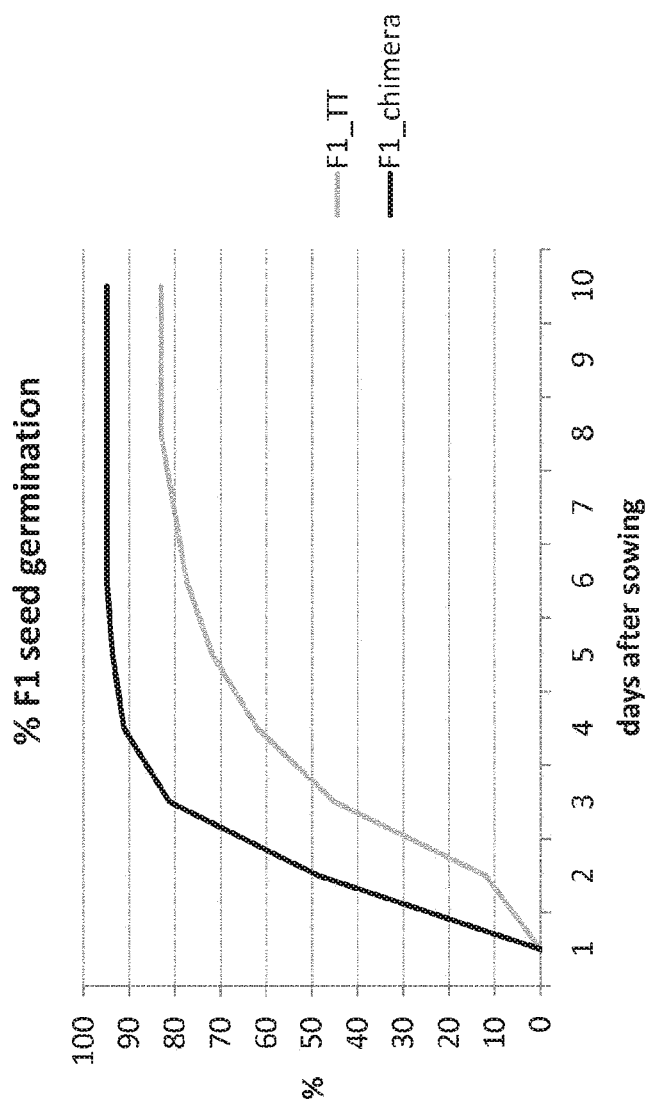
FIG. 7: In vitro germination capacity. Top line represents F1_chimera (progeny of the cross-fertilization of the chimera with line PP), bottom line represents F1_TT (progeny of the cross-fertilization of the non-chimeric plant TT with line PP).

Germination capacity was measured in vitro in the same arrays as described under section (b) above, by scoring the total number of seeds (%) that had germinated after 10 days. Results are given in FIG. 7. Germination capacity in vitro was higher for seed of the chimera, compared to the TT control plant.

Example 4

Germination properties of tomato seeds from the interspecific F1 hybrid TH were improved. This F1 hybrid is produced by crossing a maternal inbred line TT of *S. lycopersicum* to a paternal line HH from *S. habrochaites*.

A periclinal chimera was made of type {L3 (TT), L2 (TT), L1 (EP)}, wherein TT and EP denote diploidy (where T and L1 and P are haploid). TT is a standard inbred tomato (*S. lycopersicum*) variety. EP is a first generation F1 hybrid of a standard *S. lycopersicum* inbred line EE (cv. Ailsa Craig accession LA3579), and a *S. pennellii* line PP (accession LA716). Periclinals were produced by first grafting EP scions onto TT rootstocks, followed by graft healing for 10 days. Graft junctions were then transversely cut, upon which callus growth and shoot regeneration occurred spontaneously. Among regenerated shoots, periclinal chimeras were selected visually, using the phenotypic marker xa plus high trichome density carried by EP scions. The semi-dominant marker xa, present in heterozygous condition, causes yellow leaves when present in L2 and/or L3. The chimera of the desired type was recognized by having green leaves (L2 and L3 of TT), plus a high trichome density (L1 of EP). The chimera was very stable throughout development and during propagation from rooted cuttings of axillary shoots, as judged by the complete absence of spontaneous invasions of L1 cells into L2, which would have been seen as yellow sectors in leaves and stems. The breeding behavior of the chimera was analyzed using segregation analyses of the xa marker. In 500 seedlings of the chimera, from a backcross to PP, we have not observed a single yellow seedling. These data showed that the chimera carried gametophytes exclusively from genotype T, and that the EP tissues only served a sporophytic role. Because the L1 layer is well known to give rise to the integuments of the ovule and later to the seed coat of the mature seed, the sporophytic role of EP in seed development of the chimera has been that of integuments and seed coat.

The chimera, as well as non-chimeric TT control plants were cross fertilized with pollen from *S. habrochaites* accession P1127826, denoted as HH, to produce TH hybrid seed (F1). All plants were grown in a regular greenhouse in the period April-August. Crosses were made by emasculating flowers just before anthesis, followed by pollination 1-2 days later. Seeds were harvested from ripe fruits, soaked in 0.5% HCl for 1 hour, then thoroughly rinsed under tap water, dried on filter paper and stored at ambient conditions for one to several weeks until use.

We defined and measured 4 germination properties of the seeds:
(a) specific weight
(b) germination rate
(c) germination capacity All measurements were taken in the following sequential way:

(a) Specific Weight

The density of a mature seed is a direct function of its physiological composition. It is mainly determined by the amount and the biochemical nature of metabolic compounds in endosperm and embryo, which occupy the space within the seed coat. Specific weight was determined by liquid density separation in solutions of sucrose in water. ~500 seeds were sequentially passed through 0, 200 and 400 grams sucrose per liter water in a graduated cylinder. Seeds that sank in the lighter solution were collected and taken to the next. This resulted in 4 density fractions, from low to high: 0, 200, 400 and 400+. Fractions were thoroughly rinsed in tap water and dried for at least 72 hours on filter paper at room temperature. The number of seeds per fraction was counted, and the distribution over the density fractions determined.

Figure 8:
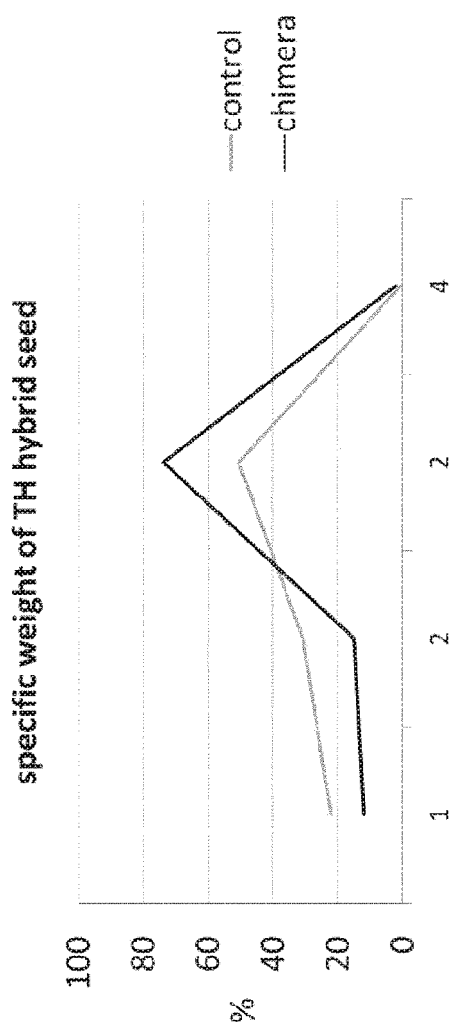
FIG. 8: Specific weight of TH hybrid seed. Black line represents F1_chimera (chimera; progeny of the cross-fertilization of the chimera with line HH), grey line represents F1_TT (control; progeny of the cross-fertilization of TT with line HH).

As shown in FIG. 8, interspecific F1 seeds made from control crosses of non-chimeric TT to HH had a density distribution different from the chimera crossed to HH. The control cross had a higher proportion of poorly filled, light seeds. Because the genotypes of embryo and endosperm in these two crosses are identical, it must be concluded that the difference in density distribution had been physiologically imparted onto the seeds by the EP sporophyte. A high proportion of poorly filled seeds is characteristic of the cross *S. lycopersicum*×*S. habrochaites*, and is a manifestation of an interspecific crossing barrier between these species. The EP sporophytic tissues in the chimeric cross corrected this.

(b) Germination Rate

Germination rate was determined in vitro by sowing batches of 100 seeds in a gridded array on moistened (tap water) filter paper in a sealed petridish, followed by incubation under 16/24 hours of white light in a climate chamber at 23 degrees Celsius. Germination was scored in 24 hour intervals as the visible emergence of a radicle, over a period of 7 days. The rate was then calculated according to the formula: rate=(#1/1)+(#2/2)+ ... +(#7/7), wherein #1 is the number of germinated seeds after 24 hours, #2 the number of germinated seeds after 48 hours, etc. The higher the rate number, the quicker the emergence of radicles. Tests were done with three 100-seed samples.

Figure 9:
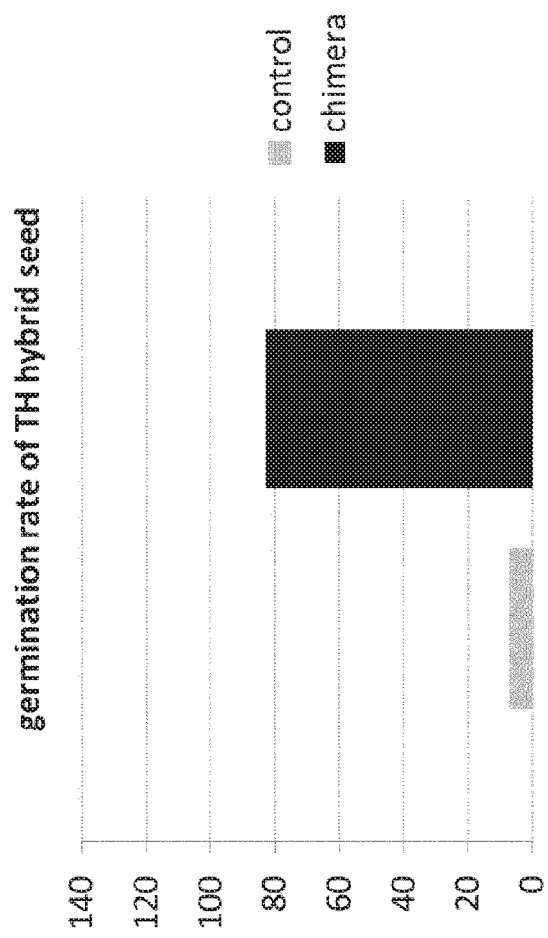
FIG. 9: Germination rate of TH hybrid seed. Black column represents F1_chimera (chimera; progeny of the cross-fertilization of the chimera with line HH), grey column represent F1_TT (control; progeny of the cross-fertilization of TT with line HH).

FIG. 9 shows the results of germination rate tests of F1 seeds produced on the chimera and on TT control plants. Only raw seeds batches were sown, i.e. they were not density fractionated before sowing. From FIG. 9 it is clear that the chimera produced seed batches with a higher germination rate. Because embryos and endosperm from the chimera and from the TT control are genetically identical, it must be concluded that the germination rate difference had been conferred physiologically by sporophyte EP. Very poor seed germination is characteristic of the cross *S. lycopersicum*×*S. habrochaites*, and is a manifestation of an interspecific crossing barrier between these species. The EP sporophytic tissues in the chimeric cross relaxed this barrier.

(c) Germination Capacity

Figure 10:
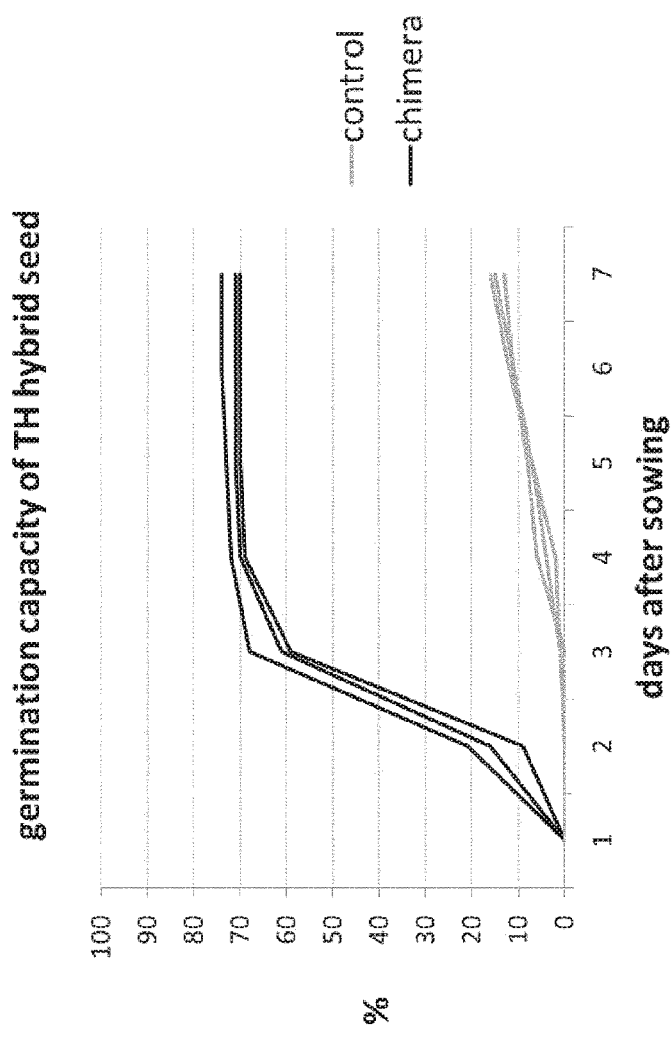
FIG. 10: In vitro germination capacity of TH hybrid seed. Black lines represent F1_chimera (chimera; progeny of the cross-fertilization of the chimera with line HH), grey lines represent F1_TT (control; progeny of the cross-fertilization of TT with line HH).

Germination capacity was measured in vitro in the same arrays as described under section (b) above, by scoring the total number of seeds (%) that had germinated after 7 days. Results are given in FIG. 10. Germination capacity in vitro was much higher for seed made on the chimera, compared to seed made on the TT control plant.

Example 5

Germination properties of inbred seeds from the beef variety BB were improved. A beef tomato variety is known in the art as a variety that has more than two, preferably more than three, locules. This variety is produced by self-fertilization of the inbred line BB of *S. lycopersicum*.

A periclinal chimera was made of type {L3 (BB), L2 (BB), L1 (ER)}, wherein BB and ER denote diploidy (where B and E and R are haploid). ER is a first generation F1 hybrid of *S. lycopersicum* inbred line EE (cv. Ailsa Craig accession LA3579), and the cherry-type *S. lycopersicum* inbred line RR. Periclinals were produced by first grafting ER scions onto BB rootstocks, followed by graft healing for 10 days. Graft junctions were then transversely cut, upon which callus growth and shoot regeneration occurred spontaneously. Among regenerated shoots, periclinal chimeras were selected by first visually identifying mericlinal yellow-green leaf chimeras using the semi-dominant phenotypic marker xa (present in the ER hybrid), followed by selection of fully green axillary branches. Green branches were genotyped with a SNP marker that distinguished BB from EE. The presence of an EE SNP indicated the shoot to be a periclinal chimera carrying an L1 layer of genotype ER over the L2 and L3 layers of BB. The chimera was very stable throughout development and during propagation from rooted cuttings of axillary shoots, as judged by the absence of spontaneous invasions of L1 cells into L2, which would have been seen as yellow sectors in otherwise green tissues.

The chimera, as well as non-chimeric BB control plants were self-fertilized. Seeds were harvested from ripe fruits, soaked in 0.5% HCl for 1 hour, then thoroughly rinsed under tap water, dried on filter paper and stored at ambient conditions for one to several weeks until use.

Germination rate was determined in vitro by sowing batches of 100 seeds in a gridded array on moistened (tap water) filter paper in a sealed petridish, followed by incubation under 16/24 hours of white light in a climate chamber at 23 degrees Celsius. Germination was scored in 24 hour intervals as the visible emergence of a radicle, over a period of 8 days. As can be seen FIG. 19, the chimera produced seeds with a strongly improved germination speed and capacity.

Example 6

Germination properties of tomato seeds from the F1 hybrid MH2 were improved. This F1 hybrid is produced by crossing a maternal inbred line MM (MoneyMaker) of *S. lycopersicum* to a paternal line H2H2 from *S. habrochaites*.

A periclinal chimera was made of type {L3 (MM), L2 (MM), L1 (EH1)}, wherein MM and EH1 denote diploidy (where M and E and H1 are haploid). EH1 is a first generation F1 hybrid of *S. lycopersicum* inbred line EE (cv. Ailsa Craig accession LA3579), and *S. habrochaites* accession P1127826.

Periclinals were produced by first grafting EH1 scions onto MM rootstocks, followed by graft healing for 10 days. Graft junctions were then transversely cut, upon which callus growth and shoot regeneration occurred spontaneously. Among regenerated shoots, periclinal chimeras were selected by first visually identifying mericlinal yellow-green leaf chimeras using the semi-dominant phenotypic marker xa (present in the EH1 hybrid), followed by selection of fully green axillary branches. Green branches were genotyped with a SNP marker that distinguished MM from EE. The presence of an EE SNP indicated the shoot to be a periclinal chimera carrying an L1 layer of genotype EH1 over the L2 and L3 layers of MM. Such chimeras could in addition be easily recognized by the distinct trichome structure of the EH1 hybrid.

The chimera was very stable throughout development and during propagation from rooted cuttings of axillary shoots, as judged by the absence of spontaneous invasions of L1 cells into L2, which would have been seen as yellow sectors in otherwise green tissues.

The chimera, as well as non-chimeric MM control plants were cross fertilized with pollen from *S. habrochaites* genotype H2 (accession LA1625) to produce MH2 hybrid seed. Crosses were made by emasculating flowers just before anthesis, followed by pollination 1-2 days later. Seeds were harvested from ripe fruits, soaked in 0.5% HCl for 1 hour, then thoroughly rinsed under tap water, dried on filter paper and stored at ambient conditions for one to several weeks until use.

Germination rate was determined in vitro by sowing batches of 100 seeds in a gridded array on moistened (tap water) filter paper in a sealed petridish, followed by incubation under 16/24 hours of white light in a climate chamber at 23 degrees Celsius. Germination was scored in 24 hour intervals as the visible emergence of a radicle, over a period of 7 days. As can be seen FIG. 20, the chimera produced seeds with a strongly improved germination speed and capacity.

Example 7

Germination properties of tomato seeds from the F1 hybrid MH2 were improved. This F1 hybrid is produced by crossing a maternal inbred line MM (MoneyMaker) of *S. lycopersicum* to a paternal line H2H2 from *S. habrochaites*.

A periclinal chimera was made of type {L3 (MM), L2 (MM), L1 (EP1)}, wherein MM and EP1 denote diploidy (where M and E and P1 are haploid). EP1 is a first generation F1 hybrid of *S. lycopersicum* inbred line EE (cv. Ailsa Craig accession LA3579), and *S. pennellii* accession LA716. Periclinals were produced by first grafting EP1 scions onto MM rootstocks, followed by graft healing for 10 days. Graft junctions were then transversely cut, upon which callus growth and shoot regeneration occurred spontaneously. Among regenerated shoots, periclinal chimeras were selected by first visually identifying mericlinal yellow-green leaf chimeras using the semi-dominant phenotypic marker xa (present in the EP1 hybrid), followed by selection of fully green axillary branches. Green branches were genotyped with a SNP marker that distinguished MM from EE. The presence of an EE SNP indicated the shoot to be a periclinal chimera carrying an L1 layer of genotype EP1 over the L2 and L3 layers of MM. Such chimeras could in addition be easily recognized by the distinct trichome structure of the EP1 hybrid.

The chimera was very stable throughout development and during propagation from rooted cuttings of axillary shoots, as judged by the absence of spontaneous invasions of L1 cells into L2, which would have been seen as yellow sectors in otherwise green tissues.

The chimera, as well as non-chimeric MM control plants were cross fertilized with pollen from *S. habrochaites* genotype H2 (accession LA1625) to produce MH2 hybrid seed. Crosses were made by emasculating flowers just before anthesis, followed by pollination 1-2 days later. Seeds were harvested from ripe fruits, soaked in 0.5% HCl for 1 hour, then thoroughly rinsed under tap water, dried on filter paper and stored at ambient conditions for one to several weeks until use.

Germination rate was determined in vitro by sowing batches of 100 seeds in a gridded array on moistened (tap water) filter paper in a sealed petridish, followed by incubation under 16/24 hours of white light in a climate chamber at 23 degrees Celsius. Germination was scored in 24 hour intervals as the visible emergence of a radicle, over a period of 7 days. As can be seen FIG. 21, the chimera produced seeds with a strongly improved germination speed capacity.

Example 8

Germination properties of tomato seeds from the F1 hybrid MP2 were improved. This F1 hybrid is produced by crossing a maternal inbred line MM (MoneyMaker) of *S. lycopersicum* to a paternal line P2P2 from *S. pennellii*.

A periclinal chimera was made of type {L3 (MM), L2 (MM), L1 (EH1)}, wherein MM and EH1 denote diploidy (where M and E and H1 are haploid). EH1 is a first generation F1 hybrid of *S. lycopersicum* inbred line EE (cv. Ailsa Craig accession LA3579), and *S. habrochaites* accession P1127826.

Periclinals were produced by first grafting EH1 scions onto MM rootstocks, followed by graft healing for 10 days. Graft junctions were then transversely cut, upon which callus growth and shoot regeneration occurred spontaneously. Among regenerated shoots, periclinal chimeras were selected by first visually identifying mericlinal yellow-green leaf chimeras using the semi-dominant phenotypic marker xa (present in the EH1 hybrid), followed by selection of fully green axillary branches. Green branches were genotyped with a SNP marker that distinguished MM from EE. The presence of an EE SNP indicated the shoot to be a periclinal chimera carrying an L1 layer of genotype EH1 over the L2 and L3 layers of MM. Such chimeras could in addition be easily recognized by the distinct trichome structure of the EH1 hybrid.

The chimera was very stable throughout development and during propagation from rooted cuttings of axillary shoots, as judged by the absence of spontaneous invasions of L1 cells into L2, which would have been seen as yellow sectors in otherwise green tissues.

The chimera, as well as non-chimeric MM control plants were cross fertilized with pollen from *S. pennellii* genotype P2 (accession LA1809) to produce MP2 hybrid seed. Crosses were made by emasculating flowers just before anthesis, followed by pollination 1-2 days later. Seeds were harvested from ripe fruits, soaked in 0.5% HCl for 1 hour, then thoroughly rinsed under tap water, dried on filter paper and stored at ambient conditions for one to several weeks until use.

Germination rate was determined in vitro by sowing batches of 100 seeds in a gridded array on moistened (tap water) filter paper in a sealed petridish, followed by incubation under 16/24 hours of white light in a climate chamber at 23 degrees Celsius. Germination was scored in 24 hour intervals as the visible emergence of a radicle, over a period of 7 days. As can be seen FIG. 22, the chimera produced seeds with a strongly improved germination speed and capacity.

Example 9

Germination properties of tomato seeds from the F1 hybrid MP2 were improved. This F1 hybrid is produced by crossing a maternal inbred line MM (MoneyMaker) of *S. lycopersicum* to a paternal line P2P2 from *S. pennellii*.

A periclinal chimera was made of type {L3 (MM), L2 (MM), L1 (EP1)}, wherein MM and EP1 denote diploidy (where M and E and P1 are haploid). EP1 is a first generation F1 hybrid of *S. lycopersicum* inbred line EE (cv. Ailsa Craig accession LA3579), and *S. pennellii* accession LA716. Periclinals were produced by first grafting EP1 scions onto MM rootstocks, followed by graft healing for 10 days. Graft junctions were then transversely cut, upon which callus growth and shoot regeneration occurred spontaneously. Among regenerated shoots, periclinal chimeras were selected by first visually identifying mericlinal yellow-green leaf chimeras using the semi-dominant phenotypic marker xa (present in the EP1 hybrid), followed by selection of fully green axillary branches. Green branches were genotyped with a SNP marker that distinguished MM from EE. The presence of an EE SNP indicated the shoot to be a periclinal chimera carrying an L1 layer of genotype EP1 over the L2 and L3 layers of MM. Such chimeras could in addition be easily recognized by the distinct trichome structure of the EP1 hybrid.

The chimera was very stable throughout development and during propagation from rooted cuttings of axillary shoots, as judged by the absence of spontaneous invasions of L1 cells into L2, which would have been seen as yellow sectors in otherwise green tissues.

The chimera, as well as non-chimeric MM control plants were cross fertilized with pollen from *S. pennellii* genotype P2 (accession LA1809) to produce MH2 hybrid seed. Crosses were made by emasculating flowers just before anthesis, followed by pollination 1-2 days later. Seeds were harvested from ripe fruits, soaked in 0.5% HCl for 1 hour, then thoroughly rinsed under tap water, dried on filter paper and stored at ambient conditions for one to several weeks until use.

Germination rate was determined in vitro by sowing batches of 100 seeds in a gridded array on moistened (tap water) filter paper in a sealed petridish, followed by incubation under 16/24 hours of white light in a climate chamber at 23 degrees Celsius. Germination was scored in 24 hour intervals as the visible emergence of a radicle, over a period of 7 days. As can be seen FIG. 23, the chimera produced seeds with a strongly improved germination speed capacity.

Example 10

Germination properties of tomato seeds from the F1 hybrid MP3 were improved. This F1 hybrid is produced by crossing a maternal inbred line MM (MoneyMaker) of *S. lycopersicum* to a paternal line P3P3 from *S. pennellii*.

A periclinal chimera was made of type {L3 (MM), L2 (MM), L1 (EH1)}, wherein MM and EH1 denote diploidy (where M and E and H1 are haploid). EH1 is a first generation F1 hybrid of *S. lycopersicum* inbred line EE (cv. Ailsa Craig accession LA3579), and *S. habrochaites* accession P1127826. Periclinals were produced by first grafting EH1 scions onto MM rootstocks, followed by graft healing for 10 days. Graft junctions were then transversely cut, upon which callus growth and shoot regeneration occurred spontaneously. Among regenerated shoots, periclinal chimeras were selected by first visually identifying mericlinal yellow-green leaf chimeras using the semi-dominant phenotypic marker xa (present in the EH1 hybrid), followed by selection of fully green axillary branches. Green branches were genotyped with a SNP marker that distinguished MM from EE. The presence of an EE SNP indicated the shoot to be a periclinal chimera carrying an L1 layer of genotype EH1 over the L2 and L3 layers of MM. Such chimeras could in addition be easily recognized by the distinct trichome structure of the EH1 hybrid.

The chimera was very stable throughout development and during propagation from rooted cuttings of axillary shoots, as judged by the absence of spontaneous invasions of L1 cells into L2, which would have been seen as yellow sectors in otherwise green tissues.

The chimera, as well as non-chimeric MM control plants were cross fertilized with pollen from *S. pennellii* genotype P3 (accession LA2657) to produce MP3 hybrid seed. Crosses were made by emasculating flowers just before anthesis, followed by pollination 1-2 days later. Seeds were harvested from ripe fruits, soaked in 0.5% HCl for 1 hour, then thoroughly rinsed under tap water, dried on filter paper and stored at ambient conditions for one to several weeks until use.

Germination rate was determined in vitro by sowing batches of 100 seeds in a gridded array on moistened (tap water) filter paper in a sealed petridish, followed by incubation under 16/24 hours of white light in a climate chamber at 23 degrees Celsius. Germination was scored in 24 hour intervals as the visible emergence of a radicle, over a period of 7 days. As can be seen FIG. 24, the chimera produced seeds with a strongly improved germination speed and capacity.

Example 11

Figure 13:
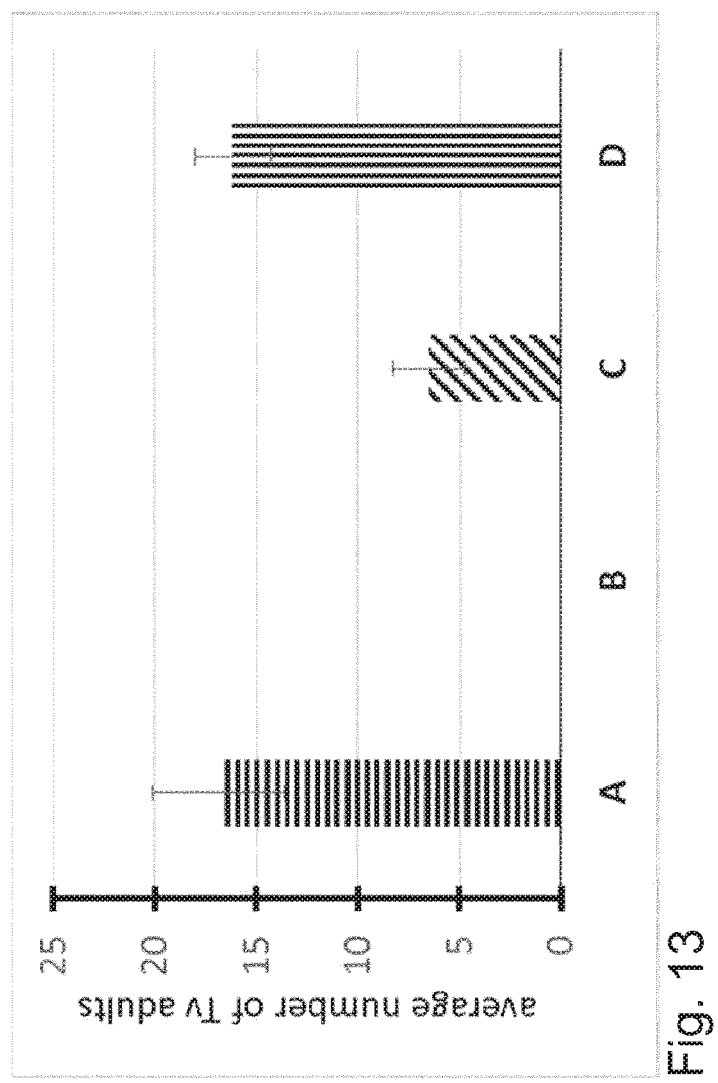
FIG. 13: Number of adult *Trialeurodes vaporariorum* on four plant genotypes (mean±stdev). A: *S. lycopersicum* (susceptible control); B: periclinal chimera with L2 and L3 from *S. lycopersicum* and L1 from F1 of *S. pennellii×S. lycopersicum* (test plant); C: periclinal chimera with L2 and L3 from *S. lycopersicum* and L1 from F1 of *S. habrochaites*×

Greenhouse whitefly (*Trialeurodes vaporariorum*; Tv) is a serious pest in tomato cultivation. F1 hybrids were created between *Solanum* pennellii accession LA716 and *Solanum lycopersicum* accession LA3579 (F1 of *S. pennellii*×*S. lycopersicum*), between *S. habrochaites* accession P1127826 and *Solanum lycopersicum* accession LA3579 (F1 of *S. habrochaites*×*S. lycopersicum*), and between *S. pimpinellifolium* accession CGN1552937 and *Solanum lycopersicum* accession LA3579 (F1 of *S. pimpinellifolium*×*S. lycopersicum*), respectively. Periclinal chimeras with an epidermis (L1) derived from each of these three F1 hybrids, and L2 and L3 derived from *Solanum lycopersicum* Moneymaker, were created using the method as detailed in Example 1. Subsequently, it was determined if periclinal chimeras show increased resistance to Tv. 30 days old cuttings of *S. lycopersicum* Moneymaker and the periclinal chimeras (two plants per genotype) were transferred to a Tv-infested greenhouse (minimum temperature of 18-20° C. at night, and maximal temperature of 25-26° C. at daytime). Three weeks after transfer of the plants, the number of alive adult whiteflies were determined (see FIG. 13). This experiment indicates that in contrast to susceptible cultivated tomato (*S. lycopersicum*), periclinal chimeras with L1 from F1 of *S. pennellii*×*S. lycopersicum* and periclinal chimera with L1 from F1 of *S. habrochaites*×*S. lycopersicum*, but not periclinal chimera with L1 from F1 of the F1 of *S. pimpinellifolium*×*S. lycopersicum*, show improved resistance to Tv. Although not shown in FIG. 13, Tv resistance in the F1 plants was tested for *S. habrochaites*×*S. lycopersicum* (mean±stdev: 16.3±11.2), and *S. pimpinellifolium*×*S. lycopersicum* (mean±stdev: 26.8±6.2).

Example 12

Thrips (*Frankliniella occidentalis*; Fo) are a serious pest in tomato cultivation. A periclinal chimera was produced as detailed in Example 1, with L1 derived from F1 of a cross of *Solanum* pennellii accession LA716 with *S. lycopersicum* accession LA3579 as L1, and L2 and L3 derived from *S. lycopersicum* Moneymaker. Subsequently, it was determined if these periclinal chimeras show increased resistance to Fo. A leaf discs bioassay was performed. In short, leaf discs of *S. lycopersicum* accession Moneymaker (susceptible control), the periclinal chimera (control plant) and the from a cross of *Solanum* pennellii accession LA716 with *S. lycopersicum* accession LA3579 (donor plant) were placed in 6-well plates, using 24 leaf discs (30 mm in diameter) from each genotype. Leaf discs were placed on top of the agar with abaxial side up. Adult *thrips* were anesthetized with $CO_2$ and one adult was put on top of each leaf disc. Each well was sealed with a Styrofoam and mesh cage. Plates were placed in a climate controlled chamber at 25° C., 60% HR and a 16 h light/8 h dark light regime. After 48 h, the adult was removed and survival was recorded. 6 days after inoculation, the number of larvae was recorded.

In contrast to susceptible control plant, the donor F1 plant and the perclinal chimera showed improved resistance to Fo (FIG. 16). Most strikingly, no Fo survived on the perclinal chimera. Furthermore, in contrast to the susceptible control plant, no progeny was observed in either the donor plant or the periclinal chimera, which indicated that no eggs were laid by female *thrips* (Table 3).

TABLE 3 number of progeny after 6 days on *S. lycopersicum* Moneymaker (susceptible control), F1 from a cross of *Solanum pennellii* accession LA716 with *S. lycopersicum* accession LA3579 (donor plant), and with L1 derived from the F1 from a cross of *Solanum pennellii* accession LA716 with *S. lycopersicum* accession LA3579 as L1, and L2 and L3 derived from *S. lycopersicum* Moneymaker (periclinal chimera).

|  | Progeny L1 |
|---|---|
| Susceptible control | 16 |
| Donor plant | 0 |
| Periclinal chimera | 0 |

Example 13

Two-spotted spider mites (*Tetranychus urticae*; Tu) are a serious pest in tomato cultivation. It is important to note that this plant pest belongs to the class of Arachnida and not Insecta.

F1 hybrids were created between *Solanum* pennellii accession LA716 and *Solanum lycopersicum* accession LA3579 (F1 of *S. pennellii*×*S. lycopersicum*), and between *S. habrochaites* accession P1127826 and *Solanum lycopersicum* accession LA3579 (F1 of *S. habrochaites*×*S. lycopersicum*), respectively. Periclinal chimeras with an epidermis (L1) derived from each of these two F1 hybrids, and L2 and L3 derived from *Solanum lycopersicum* Moneymaker, were created using the method as detailed in Example 1.

Subsequently, it was determined if periclinal chimeras show increased resistance to Tu. A leaf discs bioassay was performed. In short, leaf discs of *Solanum lycopersicum* Moneymaker (susceptible control) and the periclinal chimeras were placed in 6-well plates. Each well was filled with 6 ml of 1% technical agar. 4 plates were used per genotype. 24 leaf discs (30 mm in diameter) per genotype were used. Leaf discs were placed on top of the agar with abaxial side up. One adult spider mite was put on top of each leaf disc. Each well was sealed with a Styrofoam and mesh cage. Plates were placed in a climate controlled chamber at 25° C., 60% HR and a 16 h light/8 h dark light regime. 48 h after the adult was removed and survival was recorded. At the same time egg deposition was recorded. In contrast to susceptible control plants the periclinal chimeras showed improved resistance to Tu (Table 4 and FIG. 17).

TABLE 4 number of alive dead and percentage dead to total thrips (*Tetranychus urticae*) on *S. lycopersicum* (MM), chimeric plants (A: L2/L3 from Moneymaker and L1 from F1 of *S. lycopersicum* × *S. pennellii*); B: L2/L3 from Moneymaker and L1 from F1 of *S. lycopersicum* × *S. habrochaites*).

|  | Alive | Dead | % dead |
|---|---|---|---|
| *S. lyc* MM | 21 | 3 | 12.5 |
| A | 15 | 8 | 34.8 |
| B | 15 | 8 | 34.8 |

Example 14

Grey mold (*Botrytis cinerea*; BC) is a serious disease in tomato cultivation. This fungal pathogen causes grey mold on above-ground tissue rendering tomato fruits unmarketable. A periclinal chimera was produced as detailed in Example 1, with L1 derived from F1 of a cross of *habrochaites* accession P1127826 with *S. lycopersicum* accession LA3579 as L1, and L2 and L3 derived from *S. lycopersicum* Moneymaker. Subsequently, we determined if chimeric plants show increased resistance to Bc. A detached leaf assay was performed. In short, compound leaves of *S. lycopersicum* Moneymaker (susceptible control) and the periclinal chimera were infected with 3 uL droplets of 10E+6 spores/mL.

The average lesion diameter (mm) was determined three days after infection. We observed a significant reduction in BC lesion diameter on the periclinal chimera when compared to the disease progression in the susceptible control (FIG. 18).

Example 15

Late blight (*Phytophthora infestans*; Pi) is a serious disease in tomato cultivation. This oomycete pathogen causes disease on above-ground tissue causing severe damage to green tissue as well as tomato fruits. Periclinal chimera plants produced as detailed in Example 11 have been tested for increased resistance to Pi. A detached leaf assay has been performed. In short, leaflets of *S. lycopersicum* Moneymaker (susceptible control) and the periclinal chimeras have been infected with 3000 spores of Pi. Two droplets of 15 μl per leaflet. The average disease severity score and average lesion diameter (mm) has been determined 4 and 7 days after inoculation. At day 7, the fraction of leaves showing sporulation of Pi was determined. See Table 5.

TABLE 5 determination of disease severity caused by Pi on leaflets of chimeric plants (A: L2/L3 from Moneymaker and L1 from F1 of *S. lycopersicum* × *S. pennellii*); B: L2/L3 from Moneymaker and L1 from F1 of *S. lycopersicum* × *S. habrochaites*: C: L2/L3 from Moneymaker and L1 from F1 of *S. lycopersicum* × *S. pimpinellifolium*), donor plants and *S. lycopersicum* (MM). MM-Mock indicates uninfected control.

| genotypes | average severity score 4 dpi (0-9) | average lesion size 4 dpi (mm) | average severity score 7 dpi (0-9) | average lesion size dpi 7 (mm) | sporulation fraction 7 dpi |
|---|---|---|---|---|---|
| A | 0.3 | 0.0 | 1.3 | 2.2 | 0.0 |
| B | 0.3 | 0.0 | 0.3 | 0.0 | 0.0 |
| C | 1.0 | 0.0 | 2.0 | 3.2 | 0.2 |
| F1 of *S. lyco.* × *S. pimp.* | 5.8 | 4.2 | 7.5 | 5.0 | 0.7 |
| F1 of *S. lyco.* × *S. hab* | 0.8 | 0.0 | 1.0 | 0.5 | 0.2 |
| F1 of *S. lyco.* × *S. pen.* | 0.0 | 0.0 | 0.0 | 0.0 | 0.0 |
| MM-Mock | 0.0 | 0.0 | 0.0 | 0.0 | 0.0 |
| MM | 0.5 | 0.0 | 1.8 | 1.8 | 0.6 |

The invention claimed is:

1. A method for producing a periclinal chimera plant comprising a first L1-localized trait of interest and a second L1-localized trait of interest, the method comprising:
  (a) crossing a wild species comprising the first L1-localized trait of interest and a cultivar comprising the second L1-localized trait of interest, wherein the wild species does not comprise the second L1-localized trait of interest and the cultivar does not comprise the first L1-localized trait of interest, wherein the first L1-localized trait and the second L1-localized trait is passed to an offspring plant after crossing;
  (b) selecting a first plant comprising the first L1-localized trait of interest and the second L1-localized trait of interest from the offspring plants produced by the crossing in step (a);
  (c) providing a second plant not comprising both the first L1-localized trait of interest and the second L1-localized trait of interest; and
  (d) making a periclinal chimera plant comprising an L1-shoot meristem layer of the first plant and the L2 and L3-shoot meristem layer of the second plant, and wherein the first and second L1-localized trait of interest is selected from the group consisting of biotic stress resistance, abiotic stress resistance, improved seed germination, fruit color and the ability to accept pollen produced by the second plant or by the plant itself.

2. The method according to claim 1, wherein said first L1-localized trait of interest is a biotic or abiotic stress resistance trait, and said second L1-localized trait of interest is a fruit color trait and/or the ability to accept pollen produced by the second plant.

3. The method according to claim 2, wherein the biotic or abiotic stress resistance is selected from the group consisting of drought resistance, insect resistance, fungal resistance, oomycete resistance, level and/or composition of acylsugar production, and a combination thereof.

4. The method according to claim 1, wherein the second L1-localized trait of interest is selected from the group consisting of fruit color, ability to accept pollen that are produced by the plant itself, and a combination thereof.

5. The method according to claim 1, wherein the first plant is a commercially irrelevant plant, and wherein the second plant is of a commercially relevant variety or cultivar.

6. The method according to claim 1, wherein the first and second plant belong to the genus *Solanum*.

7. The method of claim 1, further comprising producing a plant product from the periclinal chimera plant.

8. The method according to claim 1, wherein the first plant of step (b) is an F1-hybrid of the cross of the wild species and the cultivar of step (a).

9. The method according to claim 1, wherein the method further comprises several rounds of inbreeding between step (a) and step (b) and wherein the first plant of step (b) is an inbred plant obtained by said inbreeding.

10. The method according to claim 1, wherein the second L1-localized trait of interest is the ability to accept pollen produced by the second plant.

11. The method of claim 1, wherein the second plant provided in step (c) is of the same species as the cultivar in step (a).

12. The method of claim 1, wherein the second plant provided in step (c) is of the same variety as the cultivar in step (a).

* * * * *